(12) United States Patent
Hayashi

(10) Patent No.: US 6,438,499 B1
(45) Date of Patent: Aug. 20, 2002

(54) CHROMATOGRAM ANALYZER

(75) Inventor: Hidechika Hayashi, Yokohama (JP)

(73) Assignee: Tosoh Corporation, Shinnanyo (JP)

( * ) Notice: Subject to any disclaimer, the term of this patent is extended or adjusted under 35 U.S.C. 154(b) by 0 days.

(21) Appl. No.: 09/393,194

(22) Filed: Sep. 10, 1999

(30) Foreign Application Priority Data

Sep. 10, 1998 (JP) .......................................... 10-256364
Sep. 14, 1998 (JP) .......................................... 10-260590

(51) Int. Cl.⁷ .............................................. G01N 30/86
(52) U.S. Cl. ............................................ 702/30; 702/30
(58) Field of Search ..................... 436/161; 73/23.35, 73/23.1; 364/497, 498; 235/183

(56) References Cited

U.S. PATENT DOCUMENTS

| | | | | |
|---|---|---|---|---|
| 3,555,260 A | * | 1/1971 | Karohl ......................... 235/183 |
| 3,898,837 A | * | 8/1975 | Boege ........................ 73/23.1 |
| 4,468,742 A | * | 8/1984 | Jenden et al. ................ 364/497 |
| 4,802,102 A | * | 1/1989 | Lacey ......................... 364/497 |
| 4,941,101 A | * | 7/1990 | Crilly ........................ 364/497 |
| 5,119,315 A | * | 6/1992 | Kemp et al. ................. 364/498 |
| 5,436,166 A | * | 7/1995 | Ito et al. ..................... 436/161 |
| 5,670,379 A | * | 9/1997 | Ito et al. ..................... 436/161 |
| 5,905,192 A | * | 5/1999 | Wikfors et al. ............. 73/23.35 |

OTHER PUBLICATIONS

V J Barclay, R F Bonner, and I P Hamilton; Oct. 16, 1996; Analytical Chemistry; No. 1; vol. 69; 78–90.*

* cited by examiner

*Primary Examiner*—John S. Hilten
*Assistant Examiner*—Douglas N Washburn
(74) *Attorney, Agent, or Firm*—Oblon, Spivak, McClelland, Maier & Neustadt, P.C.

(57) ABSTRACT

A chromatogram analyzer which analyzes a chromatogram obtained by applying a sample containing n analytes (wherein n is a natural number of at least 2) to chromatography to detect peaks attributable to the n analytes.

26 Claims, 12 Drawing Sheets

CHROMATOGRAM ANALYZER

BACKGROUND OF THE INVENTION

1. Field of the Invention

The present invention relates to an analyzer which analyzes a chromatogram obtained by applying a sample containing plural analytes to liquid chromatography, gas chromatography or electrophoresis using a column, a slab or the like. In particular, it relates to a chromatogram analyzer preferably used for measurement of given analytes of interest, for example, in assays of catecholamines or amino acids in a blood sample or a urine sample and in assays for quality control.

2. Discussion of Background

For chromatographic measurement of the concentrations of analytes of interest, the analytes in a sample are separated by using a liquid chromatograph, a gas chromatograph or an electrophoresis instrument and detected to give a chromatogram. Subsequently, the chromatogram is analyzed for identification of the peaks in the chromatogram attributable to individual analytes (hereinafter sometimes referred to simply as peak identification). Finally, the heights or areas of the identified peaks are determined and compared with the heights or areas of peaks chromatographically obtained from a sample containing known amounts of identical analytes under the same conditions for quantification of the analytes.

For identification of the peak attributable to a particular analyte in chromatogram analyses, it has been conventional to detect a peak within a peak detection zone between a peak detection starting time and a peak detection ending time established before and after the time at which the particular analyte is expected to emerge as a peak (the reference peak emergence time; $T_i$) by a change in the slope of the chromatogram from positive to negative or by an upturn with a slope changing from almost zero to positive and a subsequent downturn with a slope changing from negative back to almost zero in the chromatogram, or by the highest point of the chromatogram within the peak detection zone.

For identification of the peak attributable to a particular analyte, it has been conventional to fix a reference peak emergence time ($T_i$) and a duration from the peak detection starting time and the peak detection ending time ($\Delta T_i$) for the analyte and detect a peak within the peak detection zone defined by $T_i$ and $\Delta T_i$ (usually from $T_i - \Delta T_i/2$ to $T_i + \Delta T_i/2$).

In cases of identification of plural analyte peaks, each $\Delta T_i$ is usually smaller than the estimated intervals to neighboring peaks so that the peak detection zone determined for each peak does not overlap with the others.

In liquid chromatography, gas chromatography and electrophoresis, if the internal factors such as column or capillary, eluent or carrier gas composition and flow rate and the external factors such as temperature are constant, chromatograms can be obtained with good reproducibility, and the peak emergence time and the peak width for one analyte do not change a lot. Therefore, if these factors are constant, peak detection with narrow $\Delta T_i$ around $T_i$ leads to correct peak identification.

In practice, however, in chromatography, the same analyte can emerge as peaks with different shapes at different positions on chromatograms, and the actual peak emergence time can move forward or backward out of the peak detection zone for the analyte, because for example, in liquid chromatography, it is virtually impossible that the temperature, flow rate and eluent composition are always the same and because of difference in column performance among lots and change in column performance with time.

In such cases, conventional analysis methods can not identify peaks correctly, and reliable measurements are difficult. Even if a large $\Delta T_i$ (a wide peak detection zone) is fixed to allow peak detection despite a shift of the actual peak emergence time, there is a problem that correct peak identification is impossible when the actual peak emergence time for the analyte shifts by more than half of the estimated intervals to the emergence times of the neighboring peaks for some reason. Also a large $\Delta T_i$ increases the possibilities of misidentification of an interfering peak such as a ghost peak (a peak which emerges, for example, when the eluent is switched in liquid chromatography without attribution to any analyte) and a peak attributable to a contaminant as an analyte peak, and the possibilities of emergence of another analyte peak within the peak detection zone for the. analyte, and is, therefore, adverse to correct peak identification, after all.

SUMMARY OF THE INVENTION

Accordingly, the object of the present invention is to provide a chromatogram analyzer which identifies analyte peaks correctly without misidentifying ghost peaks or contaminant peaks as analyte peaks even if actual analyte peaks emerge at times different from $T_i$ to give a chromatogram different in shape and positions of peaks by various factors.

In order to achieve the above-mentioned object, according to claim 1 of the present application (hereinafter referred to as the first aspect of the present invention), the present invention provides a chromatogram analyzer which analyzes a chromatogram obtained by applying a sample containing n analytes (wherein n is a natural number of at least 2) to chromatography to detect peaks attributable to the n analytes, wherein the analyzer comprises a first storage means which stores m search sets each containing n non-overlapping peak detection zones which are defined by individual peak detection starting times and peak detection ending times (wherein m is a natural number of at least 2, and each peak detection zone for one analyte in an arbitrary search set overlaps with the peak detection zone for the same analyte in another search set); a second storage means which stores a chromatogram of the sample; a first arithmetic means which detects a peak, if any, within the peak detection zone for each of the n analytes in each search set and, if a peak is detected, matches the detected peak with the corresponding analyte, and if no peak is detected, matches no peak with the analyte to obtain identical or different peak identification results in the m search sets, and a second arithmetic means which selects one of the m peak identification results obtained by the first arithmetic means.

According to claim 4 of the present application (hereinafter referred to as the second aspect of the present invention), the present invention also provides a chromatogram analyzer which analyzes a chromatogram obtained by applying a sample containing n analytes (wherein n is a natural number of at least 3) to chromatography to detect peaks attributable to the n analytes, wherein the analyzer comprises a first storage means which stores m search sets each containing n non-overlapping peak detection zones which are defined by individual peak detection starting times and peak detection ending times (wherein m is a natural number of at least 2, and each peak detection zone for one analyte in an arbitrary search set overlaps with the peak detection zone for the same analyte in another search set); a second storage means which stores a chromatogram of the sample; a first arithmetic means which detects a peak, if any, within the peak detection zone for each of the n analytes in each search set and, if a peak is detected, matches the detected peak with the corresponding analyte, and if no peak is detected, matches no peak with the analyte to obtain identical or different peak identification results in the m search sets, and a second arithmetic means which selects one of the m peak identification results obtained by the first arithmetic means.

According to claim 21 of the present application (hereinafter referred to as the third aspect of the present invention), the present invention further provides a chromatogram analyzer which analyzes a chromatogram obtained by applying a sample containing at least three analytes, which comprises a second storage means which stores the chromatogram, a first arithmetic means which detects peaks in the chromatogram and identifies the peaks as attributable to the analytes, a third storage means which stores the reference peak emergence time of each analyte, a fourth arithmetic means which determines the indices of correlation between the stored reference peak emergence times and the emergence times of the identified analyte peaks, and a display means which displays the degree of correlation.

DETAILED DESCRIPTION OF THE PREFERRED EMBODIMENTS

Figure 1:
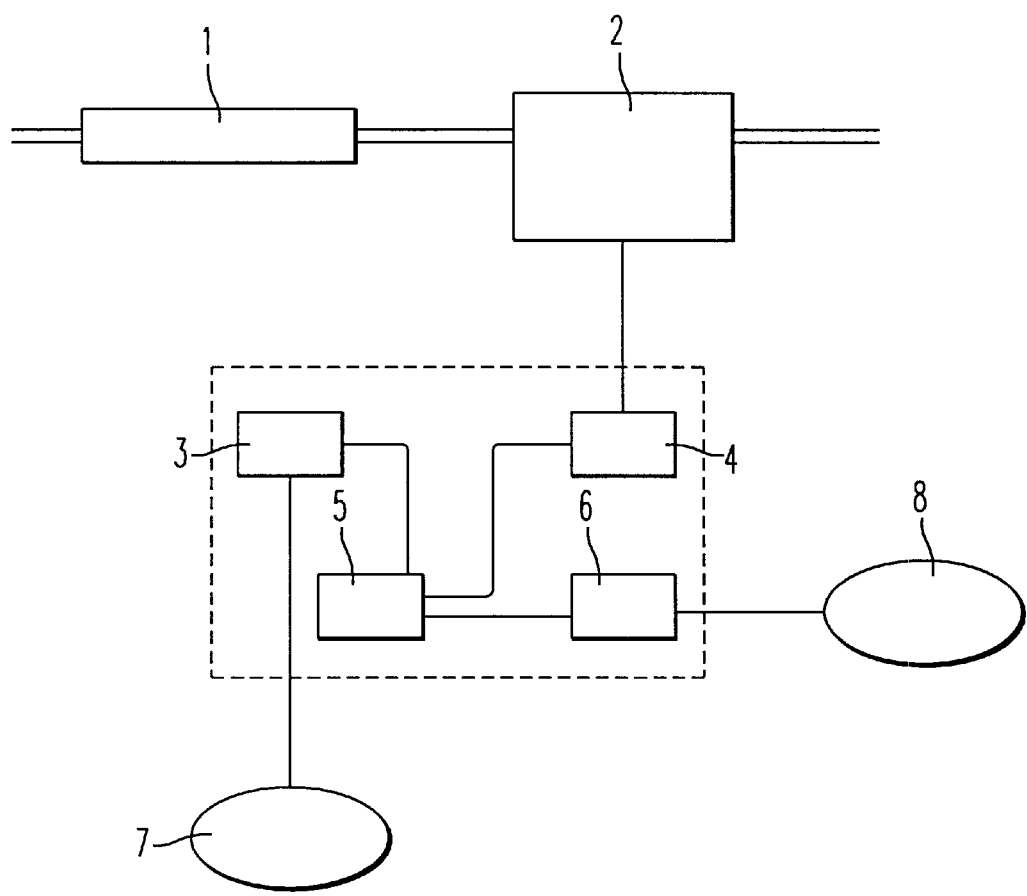
FIG. 1 is a diagram of the respective means of the chromatogram analyzer of the present invention.

Now, the present invention will be described in detail.

The chromatogram analyzer of the present invention is used for an analysis of a chromatogram developed by chromatography, namely by separating and detecting analytes in a sample. Although chromatography is divided into various types of liquid chromatography and gas chromatography according to the principles for separation and development, a chromatogram obtained by any type of chromatography can be analyzed. For example, an electrophoretically obtained result stained with a proper dye can be analyzed by using the present invention after photometric scanning. Further, the present invention is applicable to a mass spectrum analyzer by replacing the conception of time with the conception of mass number. Hereinafter, a chromatogram analyzer for liquid chromatograms is taken as an example for the sake of simple explanation.

Conventional analyzers use only one search set containing n non-overlapping peak detection zones defined by individual peak detection starting times and peak detection ending times for identification of peaks . attributable to n analytes, whereas the first aspect of the present invention is characterized in that m search sets like this (wherein m is a natural number of at least 2) are used, and in that each peak detection zone for one analyte in an arbitrary search set overlaps with the peak detection zone for the same analyte in another search set. It is also characterized in that peaks detected within the n peak detection zones in each search set are identified as attributable to the corresponding analytes to give identical or different peak identification results in the m search sets, and evaluation of these peak identification results is performed to select the most proper one. At the time of peak detection, peaks are not always detected in all of the n peak detection zones, and peak may not be detected in some of them. When no peak is detected in the peak detection zone for a particular analyte, the result of peak identification is that there is no peak matched with the analyte.

On the other hand, the second aspect of the present invention is characterized by the use of m search sets (wherein m is a natural number of at least 2) each containing n peak detection zones (wherein n is a natural number of at least 3) for identification of peaks attributable to n analytes, and in that each peak detection zone for one analyte in an arbitrary search set overlaps with the peak detection zone for the same analyte in another search set. It is also characterized in that peaks detected within the n peak detection zones in each search set are identified as attributable to the corresponding analytes to give identical or different peak identification results in the m search sets, and evaluation of these peak identification results is performed to select the most proper one. Like the first aspect of the present invention, at the time of peak detection, peaks are not always detected in all of the n number of peak detection zones, and peak may not be detected in some of them. When no peak is detected in the peak detection zone for a particular analyte, the result of peak identification is that there is no peak matched with the analyte.

The first storage means stores search sets each containing n peak detection zones (wherein n is a natural number of at least 2 according to the first aspect, and a natural number of at least 3 according to the second aspect) for detection of peaks attributable to n analytes, and may be constituted by a rewritable storage medium such as an ordinary memory or a flash memory. The number of search sets stored in the first storage means is m (wherein m is a natural number of at least 2). The number of peak detection zones contained in each search set is n, because peak detection is performed for each of the n analytes. Peak detection zones are determined so that peak detection zones for different analytes do not overlap and are stored through an external input means such as a keyboard or through another arithmetic means.

Each peak detection zone in the search sets stored in the first storage means is determined on the basis of the peak emergence time (a reference peak emergence time; $T_i$) for the corresponding analyte calculated from the chromatogram chromatographically obtained from a standard sample containing every analyte at a known concentration. The reference peak emergence times are measured preferably, but not necessarily, under the same conditions as actual measurements are done in the present invention. Peak detection zones are determined on the basis of the reference peak emergence times so that the peak detection zones in an arbitrary search set are different from the peak detection zones in other search sets. Then these peak detection zones are stored in the first storage means. For example, according to the first aspect and the second aspect of the present invention, each peak detection zone in an arbitrary search set can be determined in accordance with the after-mentioned expression by $T_i$. The intervals between emergence times of analyte peaks and the actual peak emergence times can vary due to fluctuations of internal or external factors. For example, in a case of liquid chromatography at a constant temperature with a constant eluent composition, if it is supposed that internal and external factors vary from one assay to another but are kept almost constant during one assay, changes in the intervals between peak emergence times and the peak emergence times are proportional to peak emergence times or the time gaps between the emergence time of an unretained component and peak emergence times. When a temperature gradient or an eluent gradient is employed, or when the flow path is changed by a column switch, the change in the peak emergence time of each peak is usually different. Such changes should be taken in account when the peak detection zones are determined for the m search sets stored in the first storage means.

In a specific example of the first aspect of the present invention, the centers of the n peak detection zones in each of the m search sets are given by $T_1+A_j \times \Delta T_1$, $T_2+A_j \times \Delta T_2$, $T_3+A_j \times \Delta T_3, \ldots, T_n+A_j \times \Delta T_n$ by using a real number $A_j$ (wherein j is from 1 to m, and $A_j<A_{j-1}$) wherein $A_{j+1}-A_j<1$. When the peak emergence time of a particular peak shifts opposite to other peaks due to some internal or external factors. $\Delta T_i$ is the width of the peak detection zone and is usually a positive value, but $\Delta T_i$ for some peaks may be negative. More specifically, when two search sets are provided, the centers of the peak detection zones can be defined, for example, as $T_i-\Delta T_i/6$ and $T_i+\Delta T_i/6$. In the case of three search sets, the centers of the peak detection zones can be defined, for example, as $T_i-\Delta T_i/2$, $T_i$ and $T_i+\Delta T_i/2$. Further, in the case of five search sets, the centers of the peak detection zones can be defined, for example, as $T_i-\Delta T_i$, $T_i-\Delta T_i/2$, $T_i$, $T_i+\Delta T_i/2$ and $T_i+\Delta T_i$. Once the center and the width of a peak detection zone are given, the peak detection zone is set to cover the range of $\Delta T_i/2$ before and after the center.

Although in the above-mentioned examples, the peak detection zones for one analyte are determined so as to overlap by $\Delta T_i \times 2/3$ or $\Delta T_i/2$, the overlap may be varied generally within a range of from $\Delta T_i/4$ to $\Delta T_i \times 3/4$.

According to the second aspect of the present invention, the peak detection zones for the n analytes are centered, for example, at $a_j \times T_1+b_j$, $a_j \times T_2+b_j$, $a_j \times T_3+b_j, \ldots, a_j \times T_n+b_j$ (wherein j is from 1 to m) and cover the range of $\Delta T_i/2$ before and after the centers. The centers of respective peak detection zones correspond to the respective reference peak emergence times in a chromatogram which is stretched in relation to the zero time and then shifted parallel, equivalent to those in a chromatogram stretched in relation to any time other than the zero time, and equivalent to stretched sequentially in relation to fixed times.

Namely, $a_j$ and $b_j$ in each search set are defined so as to be different from those in other search sets. However, in any case, $a_j$ is a real number close to 1, and $b_j$ is a real number selected from a range including zero.

In particular, when $a_j$ is 1 with respect to any j, the centers of the respective peak detection zones in each search set are given by $T_1+b_j$, $T_2+b_j$, $T_3+b_j, \ldots, T_n+b_j$ which means that the centers of the peak detection zones in an arbitrary search set are given only by a parallel shift of those in another search set with no change in the positional relations (with the relative positions maintained). In particular, when $b_j$ is 0 with respect to any j, the centers of the respective peak detection zones in each search set are given by $a_j \times T_1$, $a_j \times T_2$, $a_j \times T_3, \ldots, a_j \times T_n$ which means that the centers of the peak detection zones in an arbitrary search set are given only by stretching the centers of peak detection zones in another search set in relation to the zero time with the relative positions maintained. Thus, according to the second aspect of the present invention, the peak detection zones in the search sets are determined in preparation against cases of a parallel shift, a stretch or a stretch followed by a parallel shift of the emergence times of analyte peaks with no change in the positional relations of the emergence times of the analyte peaks. The coefficient $a_j$ is preferably within a range of about from 0.7 to 1.3, more preferably about from 0.8 to 1.2. On the other hand, in general, the coefficient $b_j$ is preferably about from 10 to 15% of the time required for all the analytes to be eluted.

Determination of the coefficients $a_j$ and $b_j$ will be explained further with reference to more preferable examples.

When there is only one factor that affects chromatograms, because a chromatogram is usually expected to stretch in relation to one point (r) other than the zero time, the center of each peak detection zone is expressed by $(1+p(j-(m+1)/2))$ $(T_i-r)+r$ (wherein p and q are real numbers, and j is from 1 to m). Herein the coefficients $a_j$ and $b_j$ are given by $a_j=1+p(j-(m+1)/2)$ and $b_j=p(j-(m+1)/2)$ $(-r)$.

When there are two factors that affect chromatograms, because a chromatograms is usually expected to stretch in relation to one point (r) other than the zero time and then stretch in relation to one point (s) other than the zero time, the center of each peak detection zone is expressed by $(1+q(u-(m+1)/2))$ $((1+p(t-(m_1+1)/2))$ $(T_i-r)+r-s)+s$ (wherein p and q are real numbers, t is from 1 to m, and u is 1 to $m_2$). Herein, when $m=m_1 \times m_2$ and $j=(t-1) \times m_2+u$, since j is an integer of from 1 to m, the coefficients $a_j$ and $b_j$ are given by $a_j=(1+q(u-m_2+1)/2))(1+p(t-(m_1+1)/2)$ and $b_j=(1+q(u-m_2+1)/2))p(t-(m_1+1)/2)$ $(-r)+q(u-m+1)/2)$ $(-s)$ When there are three factors that affect chromatograms, a chromatogram is usually expected to stretch in relation to one point (r) other than the zero time, then stretch in relation to one point (s) other than the zero time and further in relation to the third point other than the zero time. However, the stretch in relation to the third point other than the zero time can be expressed by the combination of the stretch in relation to the first point (r) and the stretch in relation to the second point (s). Therefore, it is possible to determine the coefficients $a_j$ and $b_j$ by taking the two factors that are more dominant on chromatograms from the three factors as if there are only two affecting factors. When the effect of the third factor is not small enough as compared to those of the first and second factors, it is preferred to broaden the overall search range so that the effect of the third factor can be expressed by the combination of the first and second factors. For example, the parameters p, q, $m_1$ and $m_2$ are preferably set at larger values in view of the third factor.

When there are four or more factors that affect chromatograms, it is possible, like in the case of three factors, to determine the coefficients $a_j$ and $b_j$ by taking the two factors that affect chromatograms more as if there are only two affecting factors. According to the first aspect and second aspect of the present invention, the width of each peak detection zone $\Delta T_i$ can be defined, for example, as $\Delta T_i = \alpha \times T_i + \beta$ (wherein $\alpha$ and $\beta$ are coefficients) so as to be smaller than the difference between the reference peak emergence times of neighboring two peaks ($T_{i+1} - T_i$ or $T_i - T_{i-1}$). When the change in each peak emergence time due to internal or external factors is proportional to the peak emergence time, $\Delta T_i$ can be defined as $\Delta T_i = \alpha \times T_i$. When the change in each peak emergence time due to internal or external factors la is about the same, or when multiple peaks which emerge at about the same time are dealt with, $\Delta T_i$ can be defined as $\Delta T_i = \beta$. Further, when the intervals of neighboring peaks are relatively small, the width $\Delta T_i$ of each peak detection zone in all the search sets is fixed, for example, at the minimum. When the change in each peak emergence time due to internal or external factors is expressed faithfully as a stretch in relation to one point (r) other than the zero time, it is preferred, for example, to diminish $\Delta T_i$ and increase the number of search sets in order to broaden the overall search range. On the other hand, when the peak intervals are large enough, or when there is no regularity in changes of respective peak emergence times, it is preferred, for example, to broaden $\Delta T_i$ and decrease the number of search sets. When the throughput of the first arithmetic means is satisfactorily large, it is particularly preferred to provide a large number of search sets and reduce $\Delta T_i$ around to several times the normal fluctuation in peak detection times. Herein, the normal fluctuation means the fluctuation in peak detection times which is not avoidable even if the internal and external environments are controlled to keep constant. The reduction of $\Delta T_i$ prevents appearance of a peak detection zone containing more than one peak and avoids wrong peak identification due to contaminants or ghost peaks when combined with the selection of one result by using an evaluation function.

The number of search sets and the widths of detection zones should be determined by taking into account the estimated fluctuation in the peak emergence times of the analyte peaks. In order to keep the overall search range unchanged, if the peak detection zones for one analyte in respective search sets are fixed at the same small value, a large number of search sets has to be provided. The same applies in cases where the overlaps between peak detection zones in different search sets are large. For example, for analysis of a chromatogram obtained by a liquid chromatographic separation of norepinephrine (NE), epinephrine (E) and dopamine (DA) according to the second aspect of the present invention, it is preferred, to the present inventors' knowledge, to provide about from 5 to 21 search sets for one affecting factor, and about from 5×5 to 21×21 search sets for two affecting factors, each containing individual peak detection zones for the analytes, NE, E and DA (wherein $\Delta T_i$ in each peak detection zone is about from 5 to 30 seconds) which cover the range of from 0.9 to 2.1 minutes for NE, the range of from 1.6 to 2.7 minutes for E and the range of from 4.2 to 4.6 minutes for DA as a whole against the factors of flow rate and temperature in the case of analysis of a chromatogram obtained from a standard sample, and cover the range of from 0.4 to 0.7 minutes for NE, the range of from 0.5 to 1.2 minutes for E and the range of from 0.9 to 3.2 minutes for DA as a whole against the factors of flow rate and temperature in the case of analysis of a chromatogram obtained from an unknown sample.

$\Delta T_i$ of each peak detection zone in one search set does not have to be the same and may be different from one analyte to another. Also, $\Delta T_i$ of each peak detection zone for an analyte in different search sets does not have to be the same and may be defined, for example, as $\Delta T_i = \alpha_k \times T_i + \beta_k$ (wherein $\alpha_k$ and $\beta_k$ are coefficients) for the kth search set.

As described above, the m search sets stored in the first storage means comprise m peak detection zones for each analyte and allow peak identification in any peak detection zone usually having a different central time (or different peak detection starting and ending times) even if a different chromatogram is obtained.

The second storage means in the present invention stores the chromatogram to be analyzed. It may be constituted by a rewritable storage medium such as an ordinary memory or a flash memory as long as it can store a detection signal from the detector in liquid chromatography in real time. The second storage means may be unified with the above-mentioned first storage s means. The real time signal storage may be done continuously or intermittently, for example, every second.

When a chromatogram is stored intermittently, the time interval for storage is preferably well shorter than peak widths. The zero time to be stored may be the time at which a sample is applied to a separation means such as a separation column or the time at which storage of the detection signal is started a certain time after the sample application. when a result of electrophoresis is scanned, migration distance is used instead of time.

The second storage means may perform smoothing by simple running averaging, polynomial fitting, the Fourier transform or a wavelet transform, or spike noise removal by simple spike removal, the Fourier transform or a wavelet transform on the stored chromatogram before identification of each analyte peak. Of course, it is possible to perform spike noise treatment and then smoothing. Noise removal by these processings makes the tops and bottoms of analyte peaks in chromatograms clear, and affords more reliable analysis results. The first arithmetic means may perform the above-mentioned processings on chromatograms instead of the second storage means.

The simple running average is expressed by $Y_n = \text{Sum}(X_i)/m$ (wherein Sum is a function which adds up consecutive data Xi, and m is the number of the data added). Polynomial fitting is expressed by $Y_n = \text{Sum}(K_i \times X_i)/\text{Sum}(K_i)$ (wherein Sum and $X_i$ are the same as defined above, and $K_i$ is a coefficient which is so determined as to fit the data to a quadratic or cubic expression). Smoothing by the Fourier transform comprises multiplying the Fourier transformed data in the frequency domain by a window function which cuts off high frequency components and taking the inverse Fourier transform of the product. Smoothing and spike noise removal by a wavelet transform are disclosed in Analytical Chemistry, vol. 69, No. 1, pp. 78–90, 1997. Simple spike removal may be conducted by the median method (in which the median of a series of three to five data, $Y = \text{Median}(X_i)$, is taken).

The first arithmetic means identifies each analyte peak in m search sets stored in the first storage means as described above and may be constituted by a computer. For identification of each analyte peak, peaks in the respective peak detection zones for detection of analyte peaks are detected, and the peak identification result in each search set is output to the second arithmetic means. Namely, for example, when n=3 and m=3, peaks attributable to the 1st to 3rd analytes are identified in each of the 1st to 3rd search sets. Of course, it is possible that no peaks are detected in some peak detection zones. Therefore, when n=3, as the results of peak identification in each search set, 3 or at most 2 analytes are matched to peaks.

The first arithmetic means may detect peaks in the respective peak detection zones in the same manner as conventional chromatogram analysis methods. For example, the first arithmetic means may be so constructed as to detect a peak within each peak detection zone (1) by a change in the slope of the chromatogram from positive to negative, (2) by an upturn with a slope changing from almost zero to positive, a turning point from positive to negative and a subsequent downturn with a slope changing from negative back to almost zero in the chromatogram or (3) by the highest point of the chromatogram within the peak detection zone. When the first arithmetic means is so constructed as in (1) or (2), more than one peak might be detected within one peak detection zone. In such cases, the first arithmetic means is so constructed that the highest peak or the peak of the largest area is selected from the detected peaks. Also, in cases of (1) or (2), instead of detecting peaks within each peak detection zone, it is possible to detect all peaks preliminarily, then make their attributions and select one peak from the peaks within each peak detection zone.

In cases of (3), when the highest point within a peak detection zone is at an edge of the peak detection zone, it is preferred to construct the first arithmetic means so as not to detect it as a peak.

The second arithmetic means evaluates the peak identification results obtained in the respective search sets by the first arithmetic means and selects one of them. The second arithmetic means may be constructed by using a computer and may be unified with the first arithmetic means. The second arithmetic means may be constructed so as to not only select one of the m peak identification results, but also further analyze each of the identified analyte peaks to quantify the analytes by comparing the peak heights or areas of the identified analyte peaks with reference to the results of analysis of a chromatogram obtained from a sample containing known concentrations of the analytes. The evaluation function used by the second arithmetic means may be different between analysis of a standard sample and that of an unknown sample.

Between the first arithmetic means and the second arithmetic means, a third arithmetic means may be provided. The third arithmetic means judges the analytes peaks identified in the peak identification results as the input from the first arithmetic means are proper or not, and if not, cancels the matching of improper peaks with analytes. The peak identification results processed by the third arithmetic means are output to the second arithmetic means.

The third arithmetic means performs judgement of analyte peaks, for example, by comparing numerically expressed attributes of the respective analyte peaks identified in the m search sets with standard values for the numerically expressed attributes of analyte peaks, and eliminating the identities of peaks which do not satisfy the values. The comparison may be based on one attribute or a plurality of attributes The standard values may be for, for example, at least one attribute selected from the group consisting of peak emergence time, peak width, peak height and peak area. A plurality of peak attributes, such as peak width and peak height may be used for standard values.

The standard values are given from a chromatogram of a sample containing the respective analytes beforehand. Because the internal and external factors causing changes in peak width, peak height, peak area and the like vary every moment, it is preferred to obtain a chromatogram of a standard sample at a certain time interval and renew the standard values used to evaluate the values for unknown samples by the third arithmetic means. Peak height determination may be performed, for example, by providing a baseline for each peak and measuring the distance from the baseline to the peak top.

More specifically, the third arithmetic means may use a standard value for peak width such as half width (the width of a peak at half the height of the peak), fifth width (the width of a peak at one fifth of the height of the peak) or tenth width (the width of a peak at one tenth of the height of the peak), without any restriction. The numerically expressed attributes of the peaks detected by the first arithmetic means are compared with the standard values for the corresponding analytes, and when numerical values expressing attributes of detected peaks are significantly different from the standard values, the peaks are judged as ghost peaks or contaminant peaks, and the matching of the peaks with analytes is cancelled. For example, numerical values which are not within ±40% of the standard values or between the predetermined upper and lower limits of peak width are considered as significantly different from the standard values.

The third arithmetic means in the chromatogram analyzer of the present invention may use different reference values, for example, reference values of peak width for analysis of a chromatogram of a standard sample containing known analytes and for analysis of a chromatogram of a sample which may or may not contain analytes. Herein the standard sample means a sample containing known concentrations of analytes which is subjected to liquid chromatography or the like prior to a sample (supposedly) containing analytes. Namely, peak emergence times or peak widths on a chromatogram of a standard sample obtained by using a different apparatus or previously obtained by using the same apparatus are used as standard values to analyze a chromatogram of a standard sample, and in subsequent analyses of chromatograms of samples containing analytes, the peak emergence time or peak widths on the chromatogram of the standard sample to analyze a chromatogram of an unknown sample obtained anew are used as standard values.

Of the examples of standard values such as peak emergence time, peak width, peak height and peak area, peaks width and peak height or peak area are particularly preferably used as standard values. As peak width, half width is particularly preferably used because it is unlikely to be affected by overlaps of peaks. In an analysis of a chromatogram of a standard sample, the peak widths and heights are compared with the standard values for peak width and height for judgement. in cases of unknown samples, judgement about peak width can be done in the same manner as for a standard sample, but because the peak heights and areas depend on the concentrations of analytes (if any) in the samples, it is preferred to set the standard values for peak height or peak area in accordance with the noise in the chromatogram, then judge peaks below the standard values to be attributable to noise and cancel the matching of such peaks with analytes.

For an analysis of a chromatogram of a sample on which contaminant peaks are predicted to emerge, it is preferred to narrow peak detection zones in the search sets for detection of analyte peaks, and in addition, to strictly determine standard values for peak width or the like. For this purpose, it is particularly preferred to obtain chromatograms of a standard sample containing known concentrations of analytes at a constant interval by chromatography and renew the standard values to be used by the third arithmetic means whenever necessary based on the chromatograms. Anyway, if any external factor has changed, it is preferred to analyze a chromatogram of a standard sample with broad peak detection zones or moderate standard values for peak width or the like for determination of peak emergence times and peak widths and then analyze a chromatogram of a sample with narrow peak detection zones or strict reference values for peak width or the like.

For evaluation of the m peak identification results obtained in the m search sets and selection of one of them by the second arithmetic means, attributes of analyte peaks may be used in combination. Evaluation is preferably performed on the basis of a value given by an evaluation function which expresses the result of evaluation. For example, the second arithmetic means may be so constructed that evaluation is performed (1) on the basis of the number of matched analytes given as the output of a function, (2) on the basis of the result obtained by introducing at least one of the number of matched analyte peaks, the peak width, height or area, the correlation index for peak emergence time and the difference between the peak emergence time of each identified analyte peak and the reference peak emergence time in each of the m search sets, into an evaluation function as the variables, or (3) on the basis of the result obtained by introducing at least one of the number of matched analyte peaks, the peak width, the uniformity of height or area, the correlation index for peak emergence times and the difference between the peak emergence time of each identified analyte peak and the reference peak emergence time in each of the m search sets, into an evaluation function as the variables. As the correlation index, the correlation coefficient between the reference peak emergence times and the peak emergence times of detected peaks, or the maximum, the average, the variance or the standard deviation of the absolute gaps from the linear regression line expressing the relation between the reference peak emergence times and the peak emergence times of detected peaks, may be used.

In the cases of (2) and (3), one evaluation result can be expressed by a single evaluation function or by the combination of a plurality of evaluation functions. In the latter case, one evaluation result can be expressed by a plurality of evaluation functions, and evaluation may be repeated, or evaluation may be executed using different functions by the case. More specifically, a function having the number of analyte peaks and the uniformity of peak heights as the variables may be used for evaluation, or evaluation using a function having the number of analyte peaks as the variable to select peak identification results wherein the number of identified analyte peaks are maximum may be followed by evaluation using a function having the uniformity of peak heights as the variable.

As an example of the above-mentioned evaluation function (1), a function which outputs the number of peaks judged as analyte peaks in each search set may be mentioned. Then, the search set which maximizes the output of the function is selected. The number of peaks judged as analyte peaks is at most n, and when the number of peaks judged as analyte peaks is n in more than one search set, the peak identification result evaluated earliest is selected, for example. It is effective to perform the evaluation by the second arithmetic means only based on the number of analyte peaks when neither contaminant peaks nor ghost peaks emerge near analyte peaks. However, when contaminant peaks or ghost peaks emerge near analyte peaks like the case of assay of catecholamine in blood or urine samples, it is preferred to use the above-mentioned evaluation function (2) or (3) having peak width, height or area, the correlation index for peak emergence time and the gap from the reference peak emergence time as the variables.

When no peaks are judged as analyte peaks in any search set, possible reasons for this are that no analytes are contained in the sample, and that the chromatogram has changed so much due to some external or internal factors that it is no longer analyzable. Accordingly, in such cases, it is preferred to provide an output means connected to the second arithmetic means which displays evaluation results with an alert. The second arithmetic means is preferably connected to an output apparatus such as a display or a printer to output these evaluation results. Also, when the number of peaks judged as analyte peaks is less than n, the same applies to at least one of the n analytes.

Examples of the evaluation function include evaluation functions of the number of analyte peaks, the peak width, height or area of each analyte peak and evaluation functions of the number of analyte peaks, the peak width, the uniformity of height or area of each analyte peak. With respect to how to handle analytes matched with no peak, only values for matched analyte peaks may be substituted into the variables of an evaluation function having the number of the matched analyte peaks as variables, or values for all the analyte peaks by allotting appropriate values to unmatched analyte peaks may be substituted into the variables of an evaluation function not having the number of the matched analyte peaks as variables. As the appropriate values, the limit of peak width or height used by the third arithmetic means may be mentioned. For example, for an analysis of a chromatogram of a standard sample containing known concentration of analytes, because it is considered that the peak width of each analyte peak in a chromatogram of a standard sample is predictable to some extent and that the heights or areas of all analyte peaks are of the same order as a whole, an evaluation function which uses these elements singly or in combination is preferable. As a single element, peak width, especially half width, which is unlikely affected by the overlaps of peaks, is preferably used. When more than one element is used, it is possible to make much of one element.

Because the heights or areas of all peaks are great and of the same order, the second arithmetic means may use, for example, an evaluation function of uniformity of peak height, $(X_1 \cdot X_2 \ldots X_n) \times ((\min(X_i)/\max(X_i)))_p$ (wherein p is more than 1), where $X_i$ is the height or area of the ith peak. If the total number of components is 3, and $X_i$ is $X_{min}$, $X_{mid}$ and $X_{max}$ in increasing order, the evaluation function is $X_{min}^3 \times X_{mid}/X_{max}$ when p=2, and $X_{min}^4 \times X_{mid}/X_{max}^2$ when p=3. A power of this function has the same effect as the evaluation function, because whichever is used as the evaluation function, the same search set maximizes the evaluation function. Further, for example, when in a chromatogram of a standard sample containing known concentrations of analytes, the height or area of each analyte peak is predicted to be considerably different due to difference in sensitivity to each analyte, it is preferred to multiply peak heights or areas by coefficients into about the same values before evaluation using the evaluation function.

For analyses of chromatograms of a plurality of samples containing analytes at unknown concentrations, when it is known that the concentration of a given analyte in every sample is of the same order, the above-mentioned evaluation function can be used. On the other hand, when the analyte concentrations in different samples vary greatly, chromatograms can be analyzed by using the above-mentioned evaluation function, though with difficulty, by considering the possible ranges of the peak width, height or area predicted from the supposed concentrations of analytes. In this case, an evaluation function having peak width, the index of correlation of peak emergence time or the gap from the reference peak emergence time as variables, is preferable.

After evaluation of m identification results obtained in m search sets by using an evaluation function, the second arithmetic means selects one identification result obtained in the search set which maximizes the above-mentioned evaluation function (2) or (3) having the number of matched analyte peaks and more than one attribute of an analyte peak as the variables. The second arithmetic means may also perform evaluation using a first evaluation function of the number of matched analyte peaks within which peaks are detected and then perform evaluation using a second evaluation function to finally select one identification result.

When the chromatogram analyzer of the present invention is used for an analysis of a chromatogram, the present invention can be applied not only to the whole chromatogram but also to groups of at least two peaks obtained by dividing the chromatogram into a plurality of groups containing at least one peak according to the reference peak emergence times and the elution behavior of analytes. Division according to peak emergence times is effective especially when the chromatogram contains many peaks or when there is not good agreement in the change of peak emergence time between analytes with relatively short emergence times and analytes with relatively long emergence times. For example, analytes may be divided according to their elution behavior into acidic, neutral and basic substances, or into hydrophilic and hydrophobic substances, for example, in amino acid analyses.

The present invention is preferably applied to samples containing at least three analytes because at least three peaks are necessary in order to evaluate the correlation of peak emergence times.

The analyzer according to the third aspect of the present invention identifies analyte peaks through peak detection and then evaluates whether the peak identification result is correct or not. However, it is possible to add to the analyzer a means for determining baselines for analysis of the areas or heights of analyte peaks or a means for determining the peak heights or areas by using the baselines without any restriction.

The third storage means may be constituted, for example, by a rewritable storage medium such as an ordinary memory or a flash memory and may be unified with the above-mentioned first or second storage means. The third storage means is connected to an external input device or the like to have the reference peak emergence times of respective analytes stored in it.

The third storage means stores the reference peak emergence time of each analyte for evaluation of identified analyte peaks. As a reference peak emergence time, the time at which an analyte peak is expected to emerge is stored. As the time, the aforementioned ts, namely, the peak emergence time of each analyte calculated from a chromatogram chromatographically obtained from a standard sample containing analytes only is particularly preferably used. The fourth arithmetic means gives an index of correlation between the reference peak emergence times and peak emergence times of identified analyte peaks and may be, for example, a computer. Examples of an index of correlation include the correlation coefficient and its square. For example, the square of the correlation coefficient (r) between $X_i$ and $Y_i$ is given by $r^2=(n\times\Sigma X_iY_i-\Sigma X_i\times\Sigma Y_i)^2/(n\times\Sigma X_i^2-(\Sigma X_i)^2)(n\times\Sigma Y_i^2-(\Sigma Y_i)^2)$. Application of the reference peak emergence times and the peak emergence times of analyte peaks to the expression as $X_i$ and $Y_i$, respectively, shows good correlation, giving r=1, when the peak emergence times of analyte peaks shift parallel (move forward or backward) with the same intervals as the intervals between the reference peak emergence times, or when a chromatogram stretches along the time axis (namely, when the ratio of the interval between the peak emergence times of any two analyte peaks to the interval of the corresponding reference peak emergence times is constant). Therefore, when r=1, the peak identification result obtained by the first arithmetic means can be judged to be correct, because the shift of peak emergence times, if any, is considered to be attributable to change in the analysis environment. The criterion for judgement can be determined, for example, so that the peak identification result obtained by the first arithmetic means is usually judged to be wrong unless r>0.999 or $r^2$>0.998, though it is determined by considering the type of chromatography to which the present invention is applied (the types of means for separation and development), the kinds of analytes and variable environmental factors and their influences as a whole, or by considering a standard sample containing actual analytes and the behavior of contaminant peaks and ghost peaks as interfering peaks. As the index of correlation, for example, when the distance between the linear regression line correlating the standard peak emergence times and the peak emergence times of the analyte peaks and a point expressing the peak emergence time of an analyte peak plotted against the corresponding reference peak emergence time is defined as a gap of the peak emergence times of the analyte peaks, the maximum absolute gap, the average absolute gap, the standard deviation of the gaps or the variance of the gaps may be used. The distance between the straight line and a point may be measured vertically (parallel to the y-axis), horizontally (parallel to the-x axis) or along the perpendicular from the point to the straight line. For example, when the linear regression line is expressed as y=A+Bx, the reference peak time is $X_i$, the peak emergence time of an identified analyte peak is $Y_i$, the coefficients A and B are given as $B=(n\times\Sigma X_iY_i-\Sigma X_i\times\Sigma Y_i)/(n\times\Sigma X_i^2-(\Sigma X_i)^2)$ and $A=(\Sigma Y_i-B\times\Sigma X_i)/n$ by using $X_i$ and $Y_i$.

When the distance between the linear regression line and a point ($X_i$, $Y_i$) is measured vertically, the gap of the peak emergence time of an analyte peak is expressed as $Y_i-(A\times X_i+B)$. When the peak emergence times of analyte peaks shift parallel (move forward or backward) with the same intervals as the intervals between the reference peak emergence times, or when a chromatogram stretches along the time axis (namely, when the ratio of the interval between the peak emergence times of any two analyte peaks to the interval of the corresponding reference peak emergence times is constant), because points expressing the peak emergence times of the analyte peaks plotted against the standard emergence times align on the linear regression line to show good correlation, the maximum absolute gap was <0.02 minute even if the error in measurement of peak emergence times is considered. Therefore, for example, when the maximum absolute gap is >0.1 minute, the peak identification result obtained by the first arithmetic means is judged as wrong. The criterion for judgement can be determined, for example, so that the peak identification result obtained by the first arithmetic means is usually judged to be wrong if the maximum absolute gap is >0.1 minute, though it is determined by considering the type of chromatography to which the present invention is applied (the types of means for separation and development), the kinds of analytes and variable environmental factors and their influences as a whole, or by considering the standard sample containing actual analytes and the behavior of contaminant peaks and ghost peaks as interfering peaks.

However, when for example, in liquid chromatography, the concentrations of constituents of the eluent are changed gradually or stepwise during elution of the analytes, the present invention can not be performed without difficulty merely by using the above-mentioned index of correlation. This is because the change in the emergence times of analytes is not a mere parallel shift or a mere stretch along the time axis. Accordingly, in such cases, the resulting chromatogram may be divided at appropriate times according to the change in the constituent concentrations of the eluent to perform the present invention. Further, for example, when analytes interact with the chromatographic column through not only ion exchanging force but also hydrophobic adsorptive force in liquid chromatography, the present invention may be applied to groups of analytes divided according to the behavior to change in temperature, eluent concentration and pH.

The fourth arithmetic means may predetermine a standard correlation value for the index of correlation which is calculated as described above. with respect to the standard correlation value, the threshold is determined, for example, so as to cover the permissible range of the index of correlation. The result of comparison between the index of correlation calculated as described above and the standard correlation value is output to the display means which will be described later. The threshold may be, for example, 0.999 or 0.1 as described above.

Different reference peak emergence times and/or different standard correlation values may be used for evaluation of a standard sample containing known concentrations of analytes only and for evaluation of an unknown sample which may contain other components. For example, for evaluation of a standard sample, peak emergence times previously obtained by analyzing the standard sample by a different analyzer may be used as the reference peak emergence times, and a moderate standard correlation value may be fixed. For evaluation of an unknown sample, peak emergence times based on the results of the analyses of the standard sample in the top of the batch are used as the reference peak emergence times, and a strict standard correlation value may be given.

The display means displays or prints the index of correlation or the like calculated by the fourth arithmetic means, preferably and the result of identification of analyte peaks obtained by the first and/or second arithmetic means, too. When the fourth arithmetic means is constituted so as to compare the calculated index of correlation and the standard correlation value, the display means may also display the result of the comparison and whether the peak identification result is proper or not. Further, for example, the display means may also display or print a chromatogram stored in the second storage means or reference peak emergence times stored in the third storage means.

The analyzer of the present invention may comprise, in addition to the previously described means, an arithmetic means which determines a baseline and calculates the peak height or area for each peak when the peak identification result is judged to be correct by the analyzer of the present invention, or a means which gives a warning when the peak identification result is judged to be wrong or when no peaks are detected for some analytes The analyzer of the present invention may further comprise an arithmetic means which calculates peak heights or areas and a means which gives a warning when the index of correlation is on the boundary of judgement of a peak identification result.

The analyzer of the present invention may be constituted by a single apparatus such as a computer. In such cases, the analyzer of the present invention may be provided with a plurality of first storage means so as to select and use an appropriate one according to the kinds of analytes, or may be provided with a plurality of standard values or evaluation functions for use in the evaluation or judgement by the second and third arithmetic means so as to select and use an appropriate one.

Further, the analyzer of the present invention may comprise an output means which displays or prints out results of analyses or a means which gives an alert when no peak is detected for an analyte.

Now, the present invention will be described in further detail by referring to Examples. However, it should be understood that the present invention is by no means restricted to these specific Examples.

FIG. 1 illustrates an example of application of the present invention to a chromatogram analyzer for liquid chromatography. In the figure, 1 is a separation column, 2 is a detector, and other chromatographic devices such as a feed pump and a sample injector are omitted.

The analyzer of the present invention, enclosed with a dashed line in the figure, is constituted by one computer including various means. In the figure, 3 is a first storage means, 4 is a second storage means, 5 is a first arithmetic means, and 6 is a second arithmetic means. A third arithmetic means may be provided between the first arithmetic means and the second arithmetic means. The first storage means 3 stores input from the keyboard 7, the second storage means 4 stores output (a chromatogram) from the detector 2, the first arithmetic means 5 is connected to the first and second storage means, and the second arithmetic means is connected to the first arithmetic means. The second arithmetic means 6 outputs the result of chromatogram analysis into the printer 8.

Figure 2:
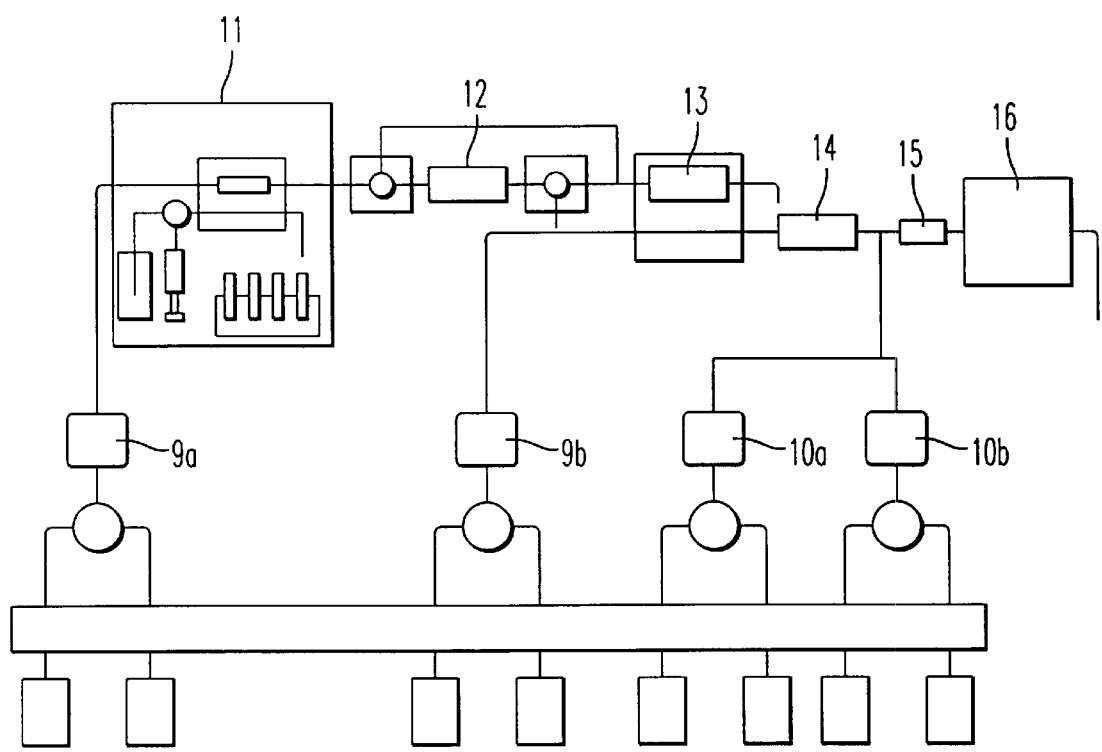
FIG. 2 is an outline of the structure of the instrument used to obtain a chromatogram of catecholamines.

FIG. 2 outlines the structure of the liquid chromatograph used in the following Examples. The chromatograph comprises eluent pumps 9a and 9b, reagent pumps 10a and 10b, an automatic sample injector 11, two pre-columns 12 and 13, an separation column 14, a reactor 15 and a fluorometric detector 16, and further an eluent switch valve and a flow switch valve. the analyzer of the present invention is connected to the detector.

Figure 3:
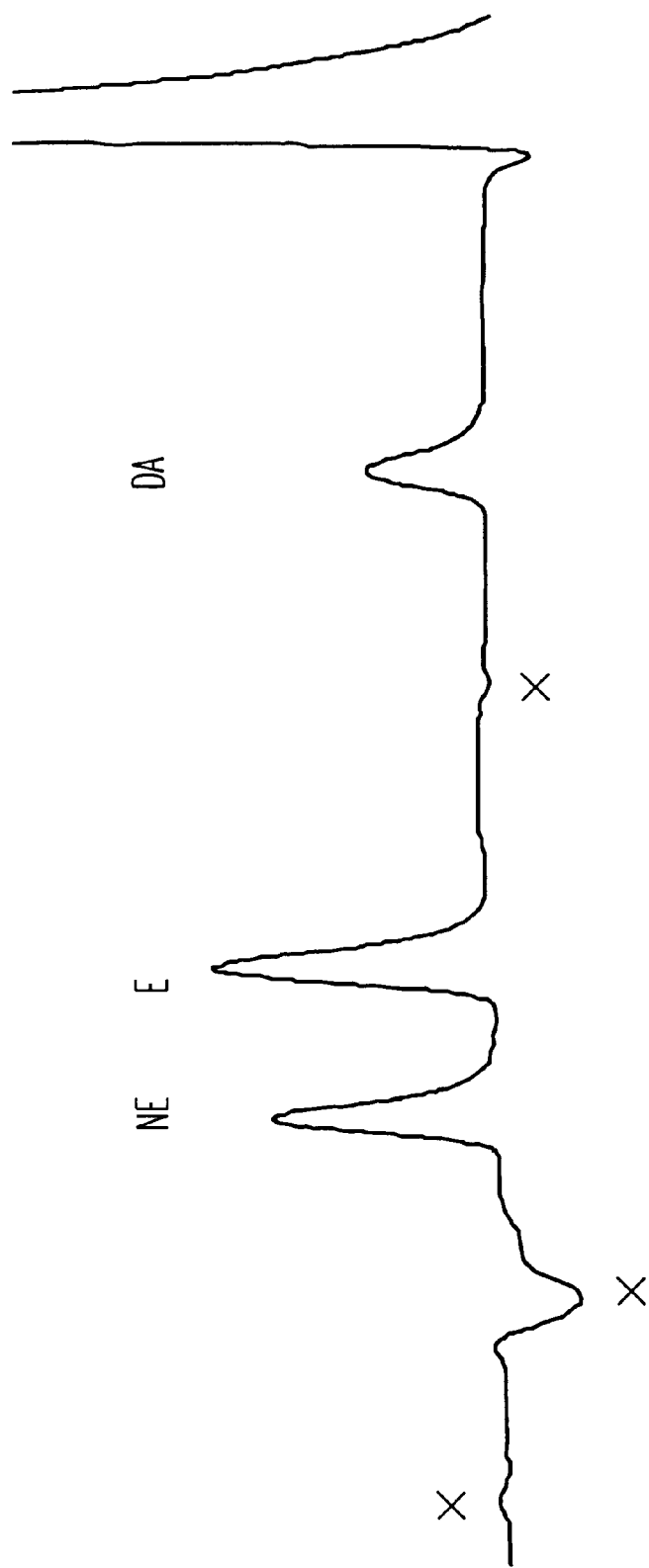
FIG. 3 is a chromatogram of a standard catecholamine sample.

FIG. 3 is a typical chromatogram obtained by applying a standard sample containing norepinephrine (NE), epinephrine (E) and dopamine (DA) at 1 pg/ml each to liquid chromatography. The peaks marked with "X" are ghost peaks, which emerged when the eluent or the flow path is switched by valve operation in the chromatograph without attribution to any analyte. The liquid is chromatograph used was equipped with two pre-columns (the first column 12 is a reversed-phase (ether gel) column of φ4.6 mm×75 mm, and the second column 13 is an ion exchange column of φ3.0 mm×60 mm) and a separation column 14 which is a reversed-phase (ODS) column (φ4.0 mm×150 mm). In the chromatograph, a sample was carried to the first pre-column by an eluent (phosphate buffer (pH 7)) fed by means of the pump 9a (1.0 ml/min), and then another eluent (a mixture of aqueous ammonium nitride and acetonitrile) was fed to the first pre-column by the pump 9a by switching a solenoid valve to elute the retained sample components onto the second pre-column. Then, the sample components retained on the second pre-column was eluted with an eluent (Tris buffer (pH 7) containing ammonium nitrate) fed by the pump 9b (0.7 ml/min) onto the separation column and separated.

The components eluted from the separation column were introduced to the reactor 15 after mixed with a fluorescent reagent and converted into a fluorescent derivative by the reaction with DPE (diphenylethylenediamine) as the fluorescent reagent at 90° C. for 3 minutes in the reactor. The fluorescent reagent was fed by means of the pump 10a and the pump 10b (0.25 ml/min each). The fluorescent derivatives of the analytes were monitored by a fluorometric detector at an excitation wavelength of 340 to 360 nm and an emission wavelength of 460 nm to give a chromatogram.

Figure 4:
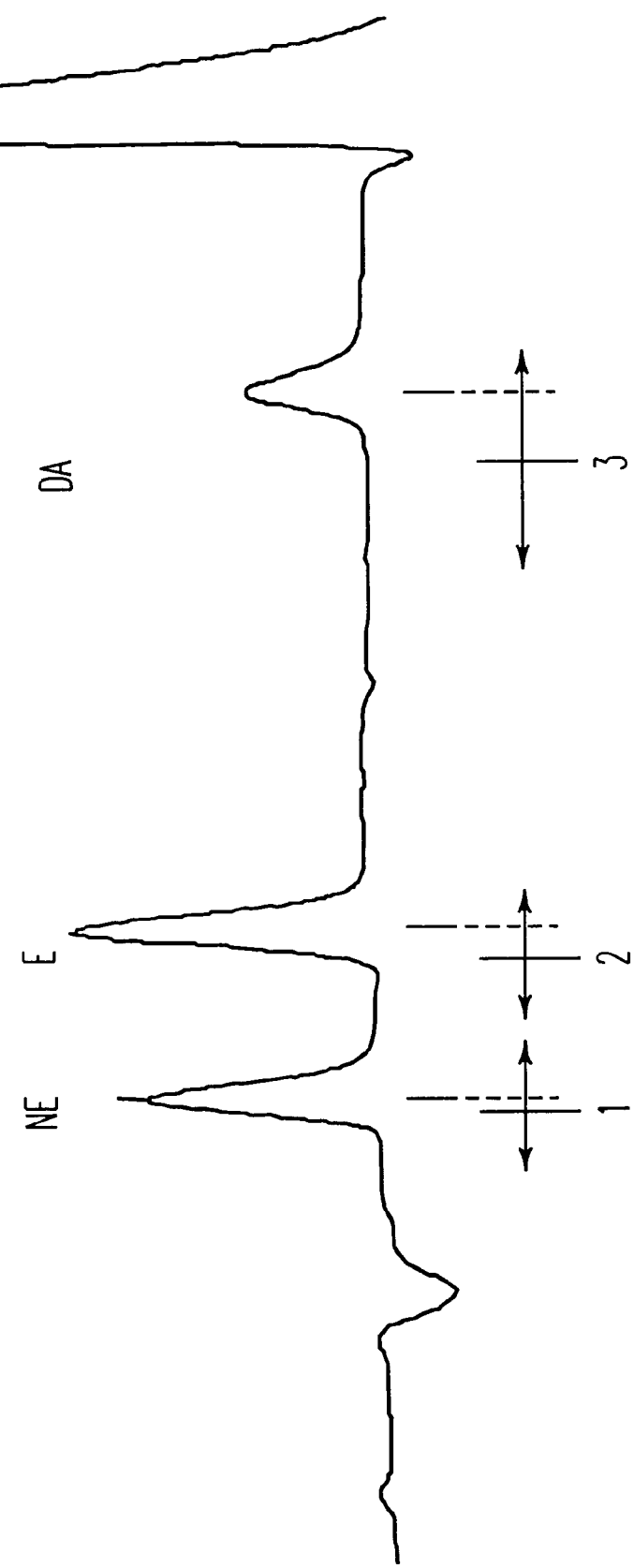
FIG. 4 is a graphic explanation of peak identification when the chromatogram has shifted (delayed).

FIG. 4 graphically shows an example of an analysis of a chromatogram of a sample containing NE, E and DA. The respective peak emergence times of NE, E and DA, 1, 2 and 3 were determined from the aforementioned chromatogram of the standard sample. The widths of the peak detection zones ($\Delta T_i$) for NE and E were defined as 80% of the interval between 1 and 2, and the width of the peak detection zone for DA was set at twice the widths of the others, because there was no peak near the DA peak. The peak detection zone for NE covers the range of $\Delta T_i/2$ before and after 1, the peak detection zone for E covers the range of $\Delta T_i/2$ before and after 2, and the peak detection zone for DA covers the range of $\Delta T_i/2$ before and after 3.

In the example of an actual chromatogram shown in FIG. 4, correct peak identification is possible because all the peaks can be detected by inclusion of the highest points within the respective peak detection zones despite the slight shifts (delays) of the peak emergence times for NE, E and DA from the peak emergence times 1, 2 and 3 with the standard sample to the positions indicated by dashed lines.

Figure 5:
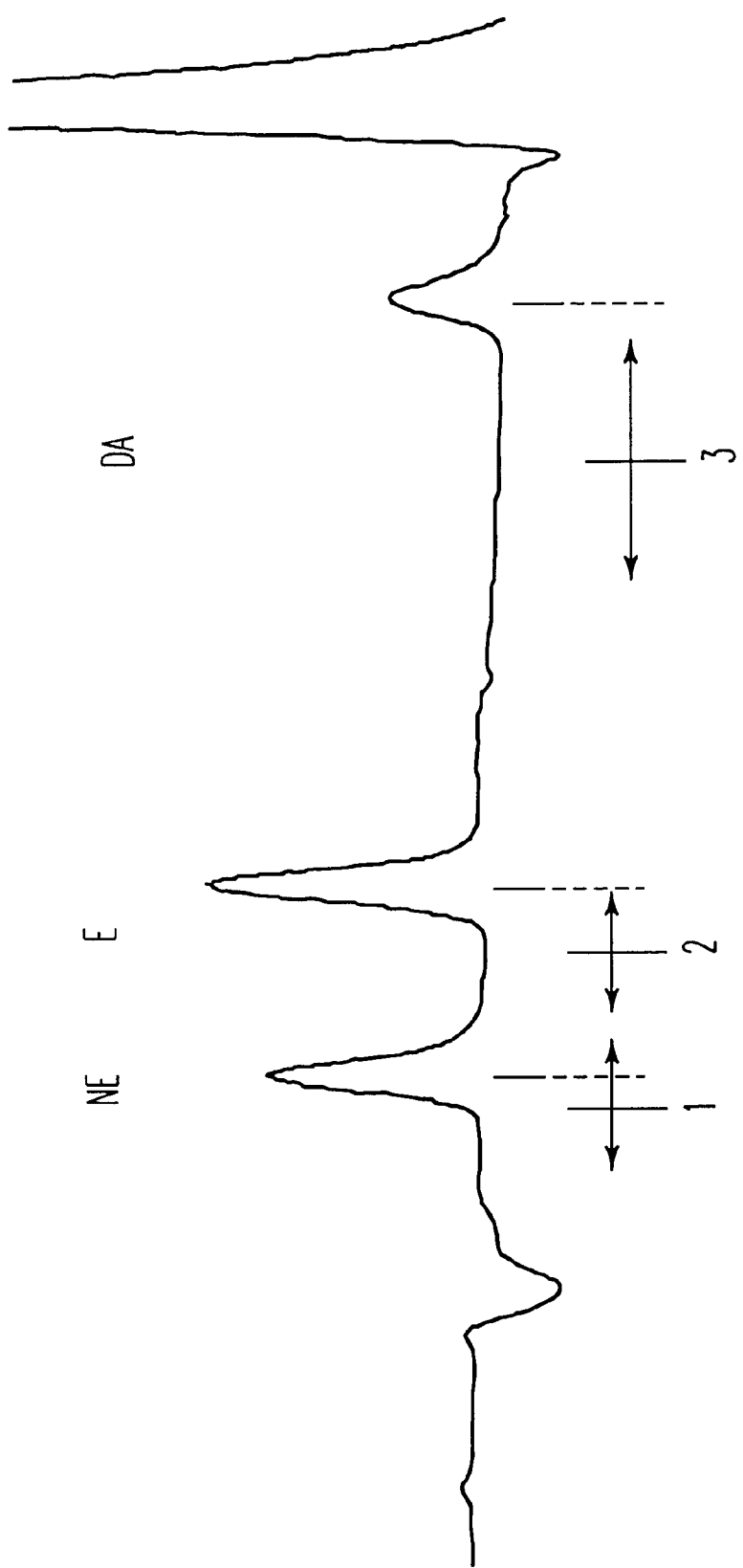
FIG. 5 is a graphic explanation of peak identification in an actual chromatogram when the chromatogram has shifted (delayed).

FIG. 5 shows an example of an actual chromatogram wherein correct peak identification is impossible because the actual peaks for E and DA are outside of the corresponding peak detection zones although the shifts (delays) of the peak emergence times for NE, E and DA from 1, 2 and 3 to the positions indicated by dashed lines are smaller than the intervals between the peaks.

Figure 6:
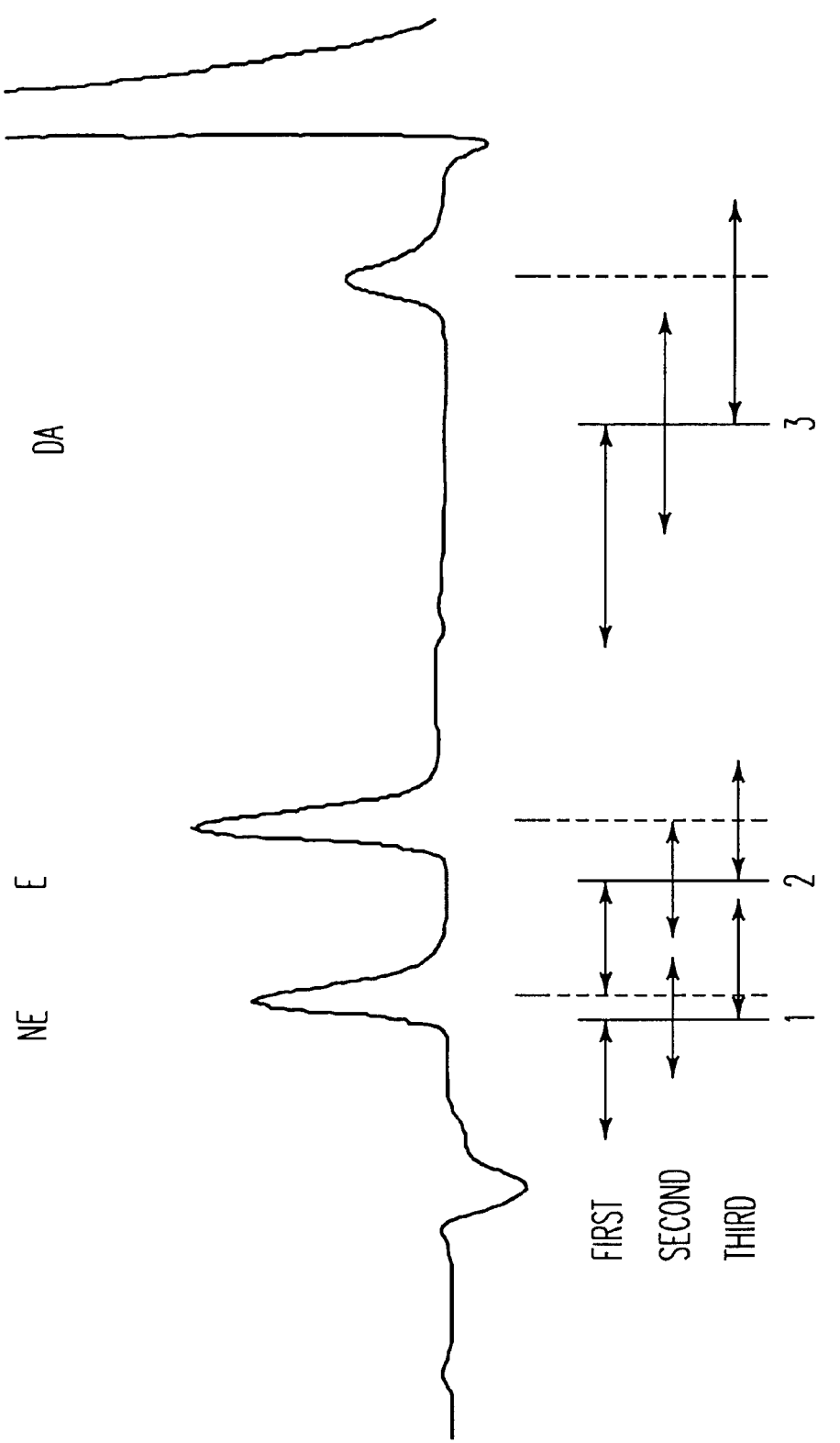
FIG. 6 is a graphic explanation of search sets in the present invention.

FIG. 6 graphically shows an example of search sets stored in the first storage means and selection of one identification result by the second arithmetic means according to the first aspect of the present invention. In this example, three search sets each containing peak detection zones for NE, E and DA, and the chromatogram shown in FIG. 5 is analyzed.

The widths of the peak detection zones $\Delta T_i$ for NE and E are defined as 80% of the interval between the peak emergence times 1 and 2 for NE and E, like in FIG. 4. The width of the peak detection zone for DA was set at twice the widths of the others, because there was no peak near the DA peak. When the peak emergence times for NE, E and DA obtained from the standard sample are represented as 1, 2 and 3, respectively, the respective peak detection starting times in the first search set are 1-$\Delta T_i$ for NE, 2-$\Delta T_i$ for E and 3$\Delta$-$T_i$ for DA, those in the second search set are 1-$\Delta T_i/2$ for NE, 2-$\Delta T_i/2$ for E and 3-$\Delta T_1/2$ for DA, and those in the third search set are 1 for NE, 2 for E and 3 for DA The first arithmetic means detects a peak within each peak detection zone by inclusion of the highest point and identifies the peak detected within the peak detection zone for NE as the NE peak, the peak detected within the peak detection zone for E as the E peak and the peak detected within the peak detection zone for DA as the DA peak.

The third arithmetic means determines the baseline and then the distance between the baseline and the highest point as the height of the peak, for each peak identified by the first arithmetic means. Then, the point at half the height and the half width are determined. The half widths thus obtained were compared with the halt widths of the NE, E and DA peaks separately calculated from the chromatogram of the standard sample shown in FIG. 3 as the reference values. The third arithmetic means performs the half width comparison by comparing the half width with the reference value for each peak, and unless the half width is within 40% of the standard value, judged identification of the analyte peak to be wrong. None of the identification results were judged to be wrong.

The second arithmetic means evaluated the peak identification results firstly by using the first evaluation function according to the number of matched analyte peaks and then performed evaluation using the second evaluation function, only with the search sets in which all analyte peaks were identified. In this example, in the first search set, no peaks were detected for NE, E and DA, and in the second search set, no peaks were detected for E and DA. Therefore, as the result of the evaluation by the second arithmetic means based on the number of matched analyte peaks, the third search set was selected. However, the second arithmetic means was constructed so as to perform evaluation using an evaluation function again to select one search set if at least two search sets were left.

The evaluation using an evaluation function was performed by using an evaluation function expressed as $X_{min}^4 X_{mid}/X_{max}^2$ wherein $X_{max}$ is the largest one of the heights of the identified NE, E and DA peaks, $X_{min}$ is the smallest one, and $X_{mid}$ is the middle one. However, it is also possible to apply the peak areas, for example, obtained by multiplying the distances between the baselines and the chromatogram of the peak by the one-tenth widths.

Figure 7:
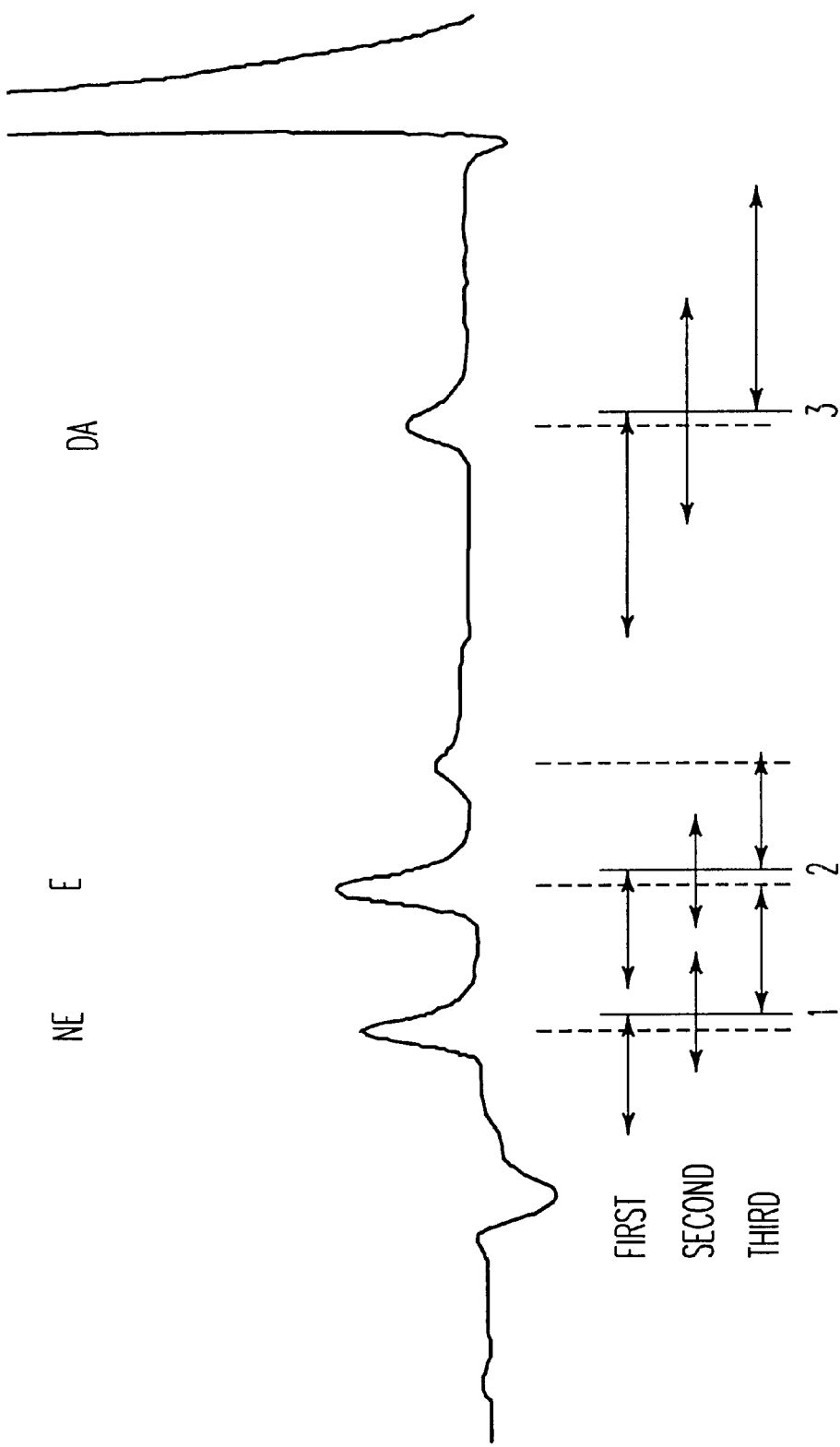
FIG. 7 is a graphic explanation of peak identification of a chromatogram using the search sets shown in FIG. 6.

FIG. 7 graphically explains an analysis of another chromatogram using the search sets shown in FIG. 6. The width of the peak detected within the peak detection zone for E and identified as the E peak in the third search set was about the same as the standard value for the width of the E peak and therefore was evaluated as a correctly identified peak as a result of comparison with the standard value by the third arithmetic means. In the third search set, no peak was detected within the peak detection zone for DA. Because the width of the peak identified as the NE peak in the first and second search sets was within ±40% of the standard value, the identity of the peak obtained in the first and second search sets were judged as correct.

Evaluation with the first and second search sets by using an evaluation function after exclusion of the third search set gave the same result. Accordingly, the second arithmetic means selected the peak identification result in the first search set on the basis of the rule that when two identification results are evaluated equally, the priority is given on the basis of the order of evaluation. In this example, because the identification results in the first and second search sets are the same, it makes no difference which one of them is selected. Actually, the same identification result can be obtained in more than one search set, because the respective peak detection zones in one search set overlap with the corresponding peak detection zones in at least one of the other search sets.

Figure 8:
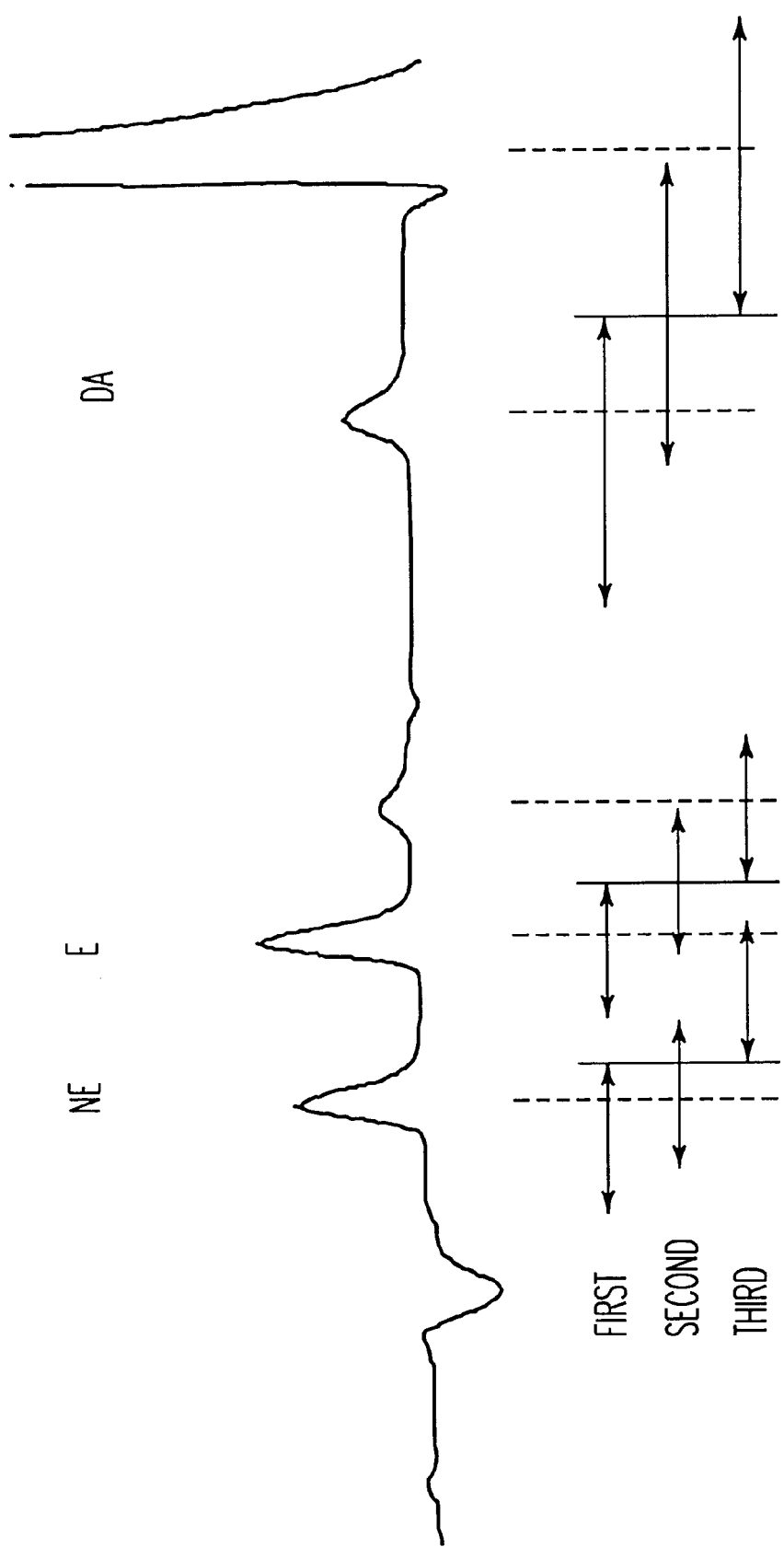
FIG. 8 is a graphic explanation of an analysis of another chromatogram using the search sets shown in FIG. 6.

FIG. 8 graphically explains analysis of another chromatogram obtained under different external conditions by using the search sets shown in FIG. 6.

In FIG. 8, the peak detected within the peak detection zone for E in the third search set was a contaminant peak, and the peak detected within the peak detection zone for DA in the third search set was a ghost peak, in fact. When the width of the ghost peak is about the same as that of the DA peak, evaluation based on the evaluation standard for peak width only leads to wrong judgement that identification of the ghost peak as the DA peak is correct. However, the second arithmetic means in the present invention evaluated the identification result in the third search set low in the evaluation step using an evaluation function on the basis of the remarkably poor uniformity of the peak heights due to the ghost peak identified as the DA peak which was much higher than the NE and E peaks and then selected the identification result in the first search set over the identification result in the second search set according to priority based on the order of evaluation.

Figure 9:
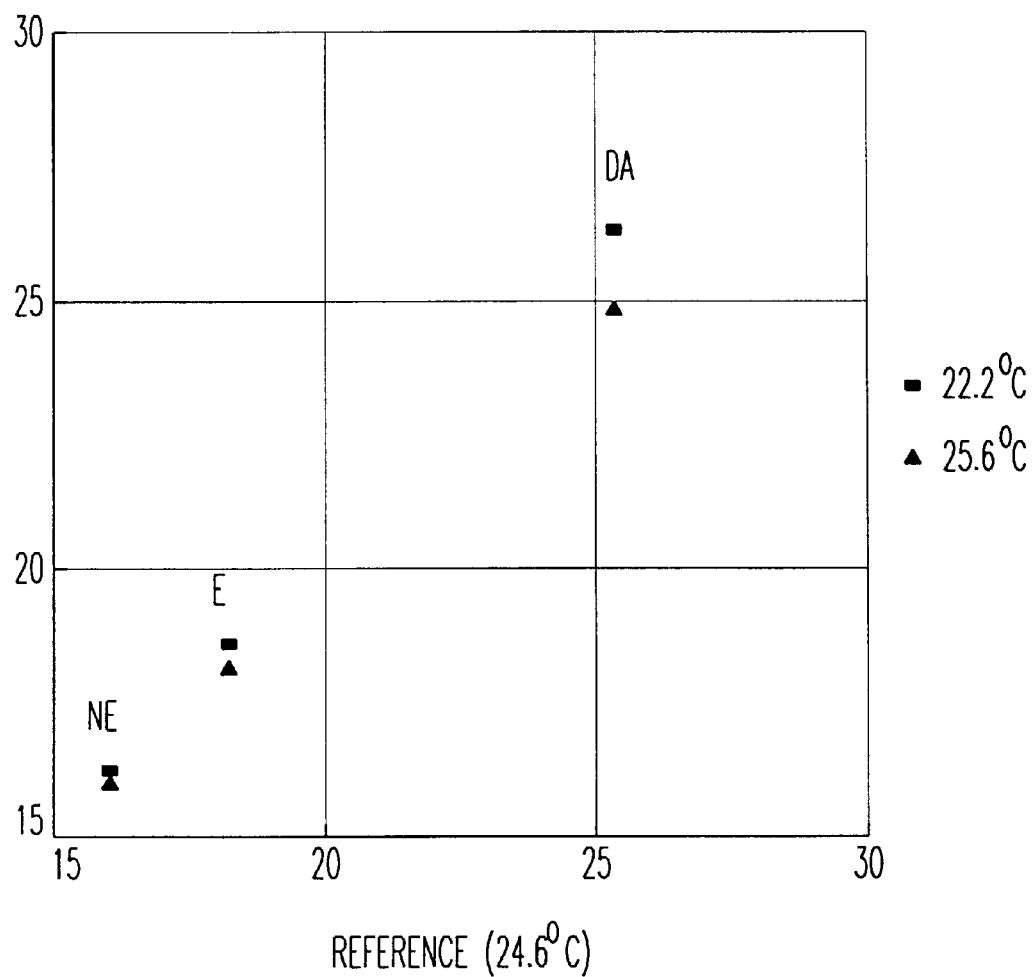
FIG. 9 is a plot of the peak emergence times of respective peaks detected in chromatograms obtained by liquid chromatography of a sample containing NE, E and DA at various temperatures.

FIG. 9 is a plot showing the relation of the peak emergence times of the respective analyte peaks obtained by liquid chromatography of a similar sample at 24.6° C. The abscissa is the peak emergence time of each analyte peak at 24.6° C. and those at 22.2° C. or 25.6° C. (reference peak emergence time), and the ordinate is the peak emergence time of each analyte peak at 22.2° C. or at 25.6° C. The points corresponding to NE, E and DA align on a straight line both at 22.2° C. and at 25.60° C., showing good correlation between peak emergence times on chromatograms obtained under different temperature conditions.

Figure 10:
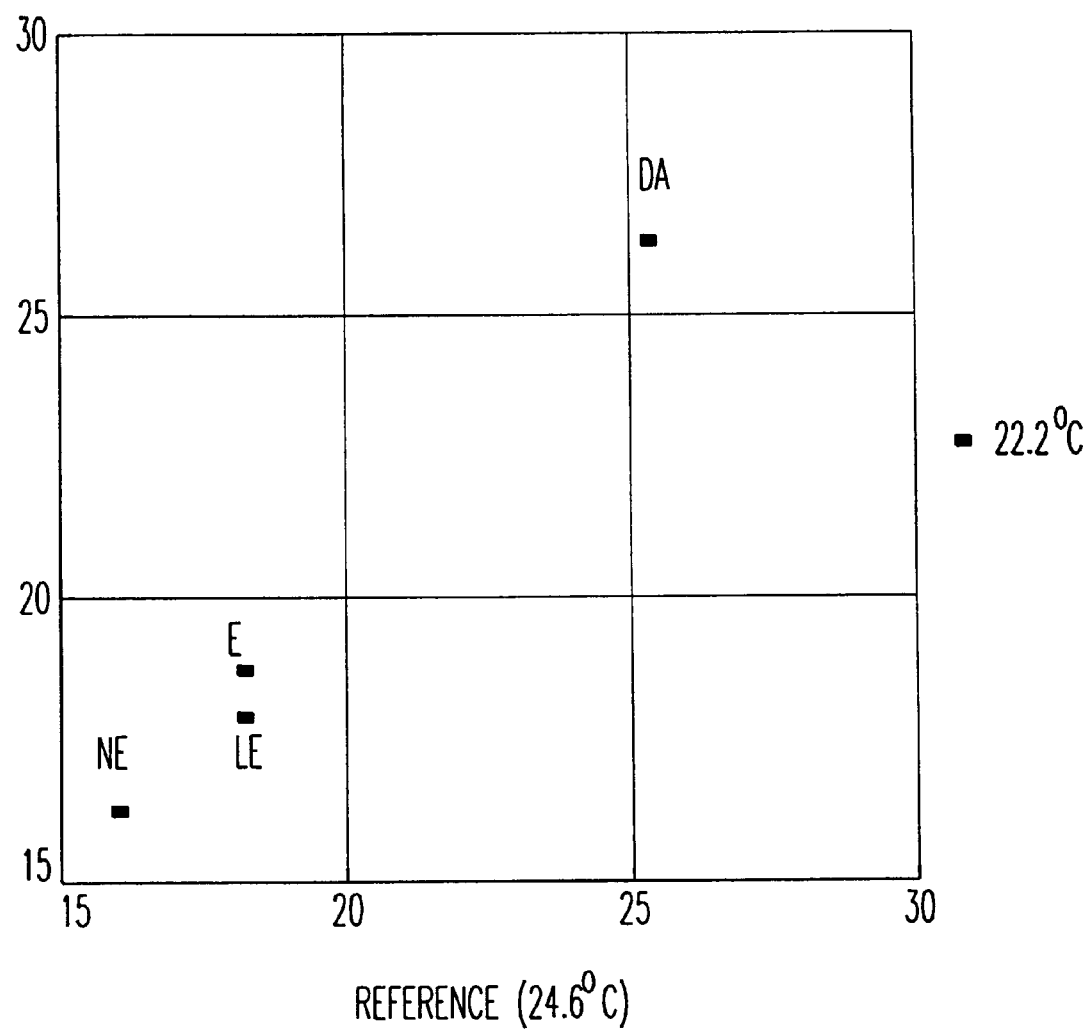
FIG. 10 is a plot the peak emergence time in liquid chromatography of a sample containing NE, E and DA, and LE as a contaminant in the same manner as previously described in FIG. 8.

The plot of peak emergence time at 24,6° C. against reference peak emergence time at 24.6° C. lay on a straight line expressed as y=x, not shown in the figure, and these three lines intersected one another at about 15 minutes, which indicates that the time axis stretches in relation to the time of 15 minutes if the chromatographic temperature changes. FIG. 10 is a plot of the peak emergence time in liquid chromatography of NE, E, DA and levonordefrin (LE) as a contaminant in a sample at 22.2° C. carried out in the same manner as previously described in FIG. 8. The peak emergence time for LE was about 17.7 minutes and close to that for E. Therefore, conventional methods may detect the LE peak after detection of the peaks in the chromatogram and misidentity the LE peak as the E peak.

Figure 11:
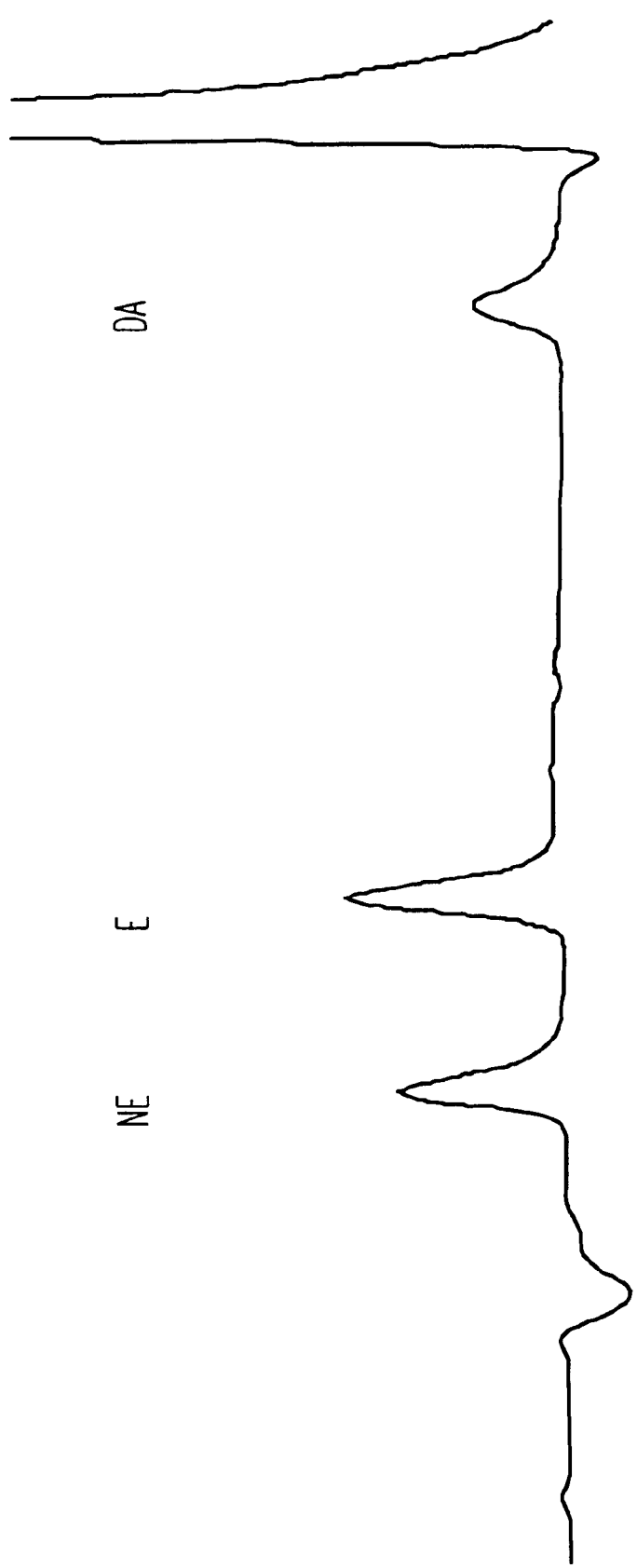
FIG. 11 is a chromatogram obtained by liquid chromatography of a sample containing NE, E arid DA at 22.2° C.
Figure 12:
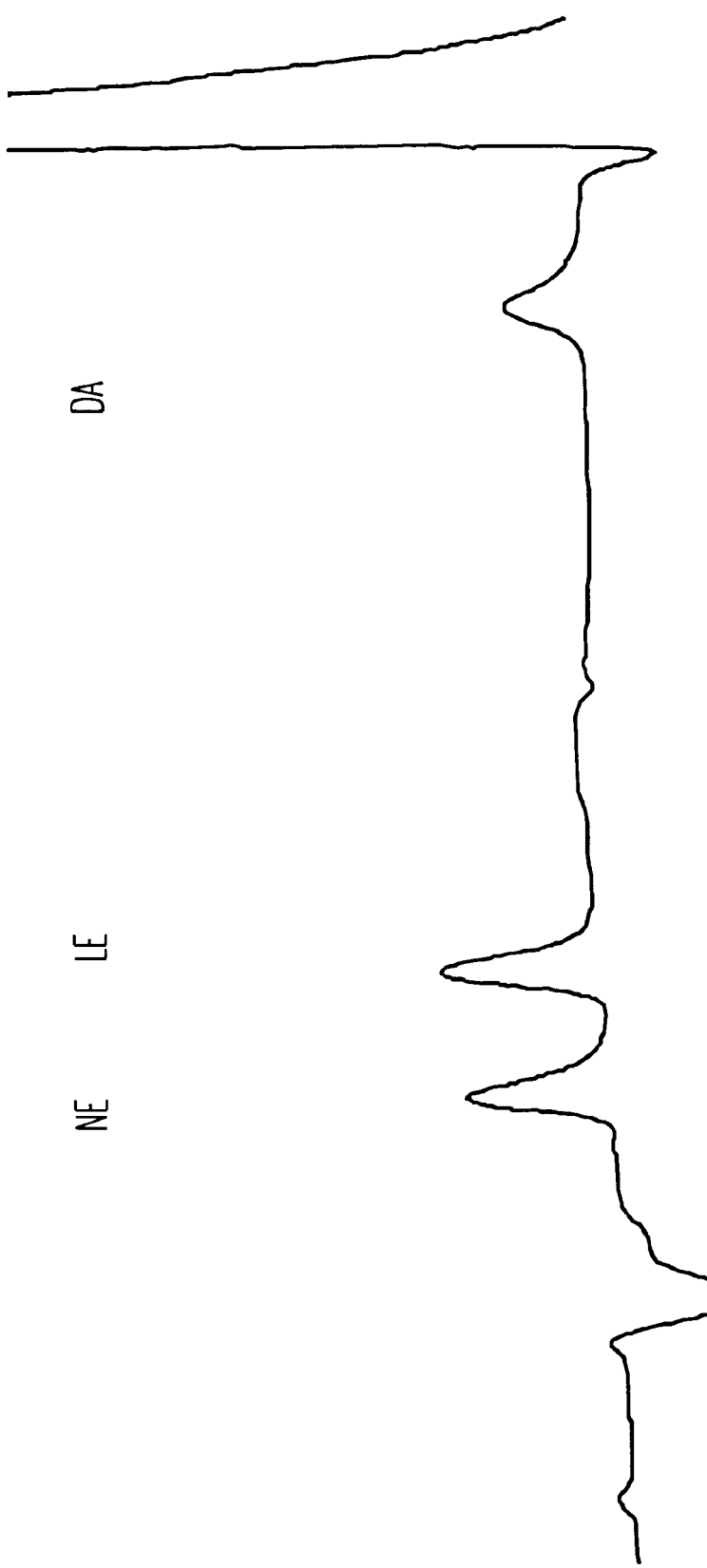
FIG. 12 is a chromatogram obtained by liquid chromatography of a sample containing NE, LE and DA under the same conditions as for FIG. 10.

FIG. 11 is a chromatogram obtained by liquid chromatography of a sample containing NE, E and DA at 22.2° C., and FIG. 12 is a chromatogram obtained by liquid chromatography of a sample containing NE, LE and DA under the same conditions. Thus, because the LE peak emerged near the E peak in the actual chromatograms, the possibility of wrong identification of the LE peak as the E peak can not be denied depending on the method of peak detection.

Table 1 shows the results of analyses of the chromatograms shown in FIG. 11 and FIG. 12 by the analyzer of the present invention. In these cases, the peak emergence times for NE, E and DA in a chromatogram obtained by liquid chromatography of a sample containing these analytes at 24.6° C. were stored in the third storage means as the reference peak emergence times. The chromatogram shown in FIG. 12 was analyzed by the analyzer of the present invention on the assumption that the LE peak was misidentified as the E peak.

TABLE 1

| Index of correlation | NE, E and DA peaks | NE, LE and DA peaks |
|---|---|---|
| Correlation coefficient | 1.0000 | 0.9960 |
| Square of correlation coefficient | 1.0000 | 0.9921 |
| Maximum | 0.0157 | 0.534 |

TABLE 1-continued

| Index of correlation | NE, E and DA peaks | NE, LE and DA peaks |
|---|---|---|
| absolute gap Average | 0.010825 | 0.356081 |
| absolute gap Standard deviation of gap | 0.011845 | 0.394407 |

As is evident from Table 1, because the peak emergence times for the respective analytes NE, E and DA in a standard sample maintain good correlation with the corresponding reference peak emergence times even when they vary depending on the temperature at which liquid chromatography is carried out, and with respect to the indices of correlation, the correlation coefficient of 1 and a quite small maximum absolute gap were obtained as the result of calculation by the second arithmetic means in the present invention. In contrast, when it was assumed that the LE peak was misidentified as the E peak in the analysis by the analyzer of the present invention, with respect of the indices of correlation, the correlation coefficient of less than 0.999 and a large maximum absolute gap were obtained as the result of calculation by the second arithmetic means. From these results, when results of identification of NE, E and DA peaks in an analysis of catecholamines are judged, it is possible to know that an identification result obtained by the first arithmetic means is wrong if the correlation coefficient calculated by the fourth arithmetic means as the index of correlation is less than 0.999, or if the maximum absolute gap calculated by the fourth arithmetic means as the index of correlation is more than 0.1 minute.

Thus, in these examples, the indices of correlation and the criteria for judgement of misidentification in the case of an analysis of catecholamines using NE, E and DA as the analytes and LE as a contaminant which causes an interfering peak are specifically explained. However, the above-mentioned thresholds may be determined by considering the kinds of analytes, the kinds of predictable contaminants and the actual chromatograms.

The present invention makes it possible to identify peaks in a chromatogram as attributable to analytes expected in the sample even if the peaks have shifted by nearly or more than the interval to a neighboring peak due to change in the external or internal factors Especially, according to the second aspect of the present invention, because search sets suitable to detection of peaks having peak emergence times in good correlation with reference peak emergence times are provided, even though a contaminant peak or a ghost peak may be identified as an analyte peak in one peak search set, it is very unlikely that while a contaminant peak or a ghost peak is detected within one peak detection zohe, all of the other analytes are matched with peaks, and therefore, correct identification can be attained.

According to the present invention, it is possible to exclude the possibilities of misidentification of a ghost peak as an analyte peak and misidentification of a peak as attributable to a neighboring analyte even if the search range is broadened. Further, according to the present invention, even when peak emergence times have considerably changed due to change of the column or the lot of the solvent, there is no need of re-establishment of the peak emergence times for an analysis of a chromatogram of a standard sample, which used to be needed.

The analyzer according to the third aspect of the present invention makes it possible to judge whether or not peaks detected by conventional detection methods are attributable to analytes even if the peak emergence times may change due to the internal or external factors, or even if an interfering peak attributable to a contaminant or a ghost peak may appear near a peak attributable to an analyte to be measured in a chromatogram. Namely, it is possible to judge whether or not results of peak identification by analyzing peaks identified as analyte peaks by conventional methods.

Consequently, it is possible to exclude the possibility of peak analysis based on misidentification of an interfering contaminant peak or a ghost peak as an analyte peak even after such misidentification. This is of great significance because various kinds of chromatography are used for quantification of traces of analytes and because the results of chromatographic quantification of traces of analytes of clinical significance (such as proteins in blood) in the field of clinical diagnosis sometimes affect treatments on patients.

The present invention is preferably applied to analyses under constant conditions of temperature and solvent composition. For analyses with gradually or stepwise changes in temperature or solvent composition, the present invention can be applied after a chromatogram is divided into a plurality of chromatograms based on time. Further, when analytes interact with r chromatographic column in liquid chromatography not only by the ion exchange effect but also by hydrophobic adsorptive effect, the present invention can be applied after a plurality of analytes are divided into groups according to their behavior.

What is claimed is:

1. A chromatogram analyzer which analyzes a chromatogram obtained by applying a sample containing n analytes (wherein n is a natural number of at least 2) to chromatography to detect peaks attributable to the n analytes, wherein the analyzer comprises:
    a first storage means which stores m search sets each containing n non-overlapping peak detection zones which are defined by individual peak detection starting times and peak detection ending times (wherein m is a natural number of at least 2, and each peak detection zone for one analyte in an arbitrary search set overlaps with the peak detection zone for the same analyte in another search set),
    a second storage means which stores a chromatogram of the sample,
    a first arithmetic means which detects a peak, if any, within the peak detection zone for each of the n analytes in each search set and, if a peak is detected, matches the detected peak with the corresponding analyte, and if no peak is detected, matches no peak with the analyte to obtain identical or different peak identification results in the m search sets, and
    a second arithmetic means which selects one of the m peak identification results obtained by the first arithmetic means.

2. The chromatogram analyzer according to claim 1, which further comprises a third arithmetic means which is connected to the output terminal of the first arithmetic means and to the input terminal of the second arithmetic means and judges whether or not the peak identification result for each analyte is proper.

3. The chromatogram analyzer according to claim 1 or 2, wherein the centers of the peak detection zones for the n analytes in the n search sets are expressed by $T_1+A_j\times\Delta T_1$, $T_2+A_j\times\Delta T_2$, $T_3+A_j\times\Delta T_3$, ..., $T_n+A_j\times\Delta T_n$ by using a real number $A_j$ (wherein j is an integer of from 1 to m, and $A_j<A_{j+1}$) wherein the standard peak emergence times at which the peaks attributable to the n analytes are estimated to emerge are $T_1$, $T_2$, $T_{31}$, ..., $T_n$ and $\Delta T_i$ is the duration from a peak detection starting time to A peak detection ending time, and $A_{j+1}-A_j<1$.

4. A chromatogram analyzer which analyzes a chromatogram obtained by applying a sample containing n analytes (wherein n is a natural number of at least 3) to chromatography to detect peaks attributable to the n analytes, wherein the analyzer comprises;
    a first storage means which stores m search sets each containing n non-overlapping peak detection zones which are defined by individual peak detection starting times and peak detection ending times (wherein m is a natural number of at least 2, and each peak detection zone for one analyte in an arbitrary search set overlaps with the peak detection zone for the same analyte in another search set),
    a second storage means which stores a chromatogram of the sample,
    a first arithmetic means which detects a peak, if any, within the peak detection zone for each of the n analytes in each search set and, if a peak is detected, matches the detected peak with the corresponding analyte, and if no peak is detected, matches no peak with the analyte to obtain identical or different peak identification results in the m search sets, and
    a second arithmetic means which selects one of the m peak identification results obtained by the first arithmetic means.

5. The chromatogram analyzer according to claim 4, which further comprises a third arithmetic means which is connected to the output terminal of the first arithmetic means and to the input terminal of the second arithmetic means and judges whether or not the peak identification result for each analyte is proper.

6. The chromatogram analyzer according to claim 4 or 5, wherein the peak detection zones for the n analytes in the m search sets are centered at $a_j\times T_1+b_j$, $a_j\times T_2+b_j$, $a_j\times T_3+b_j$, ..., $a_j\times T_n+b_j$ (wherein j is an integer of from 1 to m) wherein the standard peak emergence times at which the peaks attributable to the n analytes are estimated to emerge are $T_1$, $T_2$, $T_3$, ..., $T_n$.

7. The chromatogram analyzer according to claim 6, wherein the peak detection zones for the n analytes in the m search sets are centered at $T_1+b_j$, $T_2+b_j$, $T_3+b_j$, ..., $T_n+b_j$ (wherein j is an integer of from 1 to m) wherein the standard peak emergence times at which the peaks attributable to the n analytes are estimated to emerge are $T_1$, $T_2$, $T_3$, ..., $T_n$.

8. The chromatogram analyzer according to claim 6, wherein the peak detection zones for the n analytes in the m search sets are centered at $a_j\times T_1$, $a_j\times T_2$, $a_j\times T_3$, ..., $a_j\times T_n$ (wherein j is an integer of from 1 to m.) wherein the standard peak emergence times at which the peaks attributable to the n analytes are estimated to emerge are $T_1$, $T_2$, $T_3$, ..., $T_n$.

9. The chromatogram analyzer according to claim 1, 2, 4 or 5, wherein the first arithmetic means detects a peak within each peak detection zone by a change in the slope of the chromatogram from positive to negative.

10. The chromatogram analyzer according to claim 1, 2, 4 or 5, wherein the first arithmetic means detects a peak within each peak detection zone in the chromatogram by an upturn with a slope changing from almost zero to positive and a subsequent downturn with a slope changing from negative back to almost zero.

11. The chromatogram analyzer according to claim 1, 2, 4 or 5, wherein the first arithmetic means detects a peak within each peak detection zone by the highest point of the chromatogram within the peak detection zone.

12. The chromatogram analyzer according to claim 2 or 5, wherein the third arithmetic means judges whether or not the peak matched with each analyte is proper by comparing a numerically expressed attribute of each analyte peak with a standard value for a numerically expressed attribute of the analyte peak for the identification result obtained in each of the m search sets,: and, if the standard value is not satisfied, canceling the matching of the peak to the analyte.

13. The chromatogram analyzer according to claim 12, wherein the standard value for a numerically expressed attribute of an analyte peak is a standard value for at least one selected from the group consisting of the peak width, the peak height and the peak area of each peak.

14. The chromatogram analyzer according to claim 1, 2, 4 or 5, wherein the second arithmetic means selects one peak identification result on the basis of the result of evaluation using an evaluation function having at least one of the peak width, the peak height, the peak area of an analyte peak, the correlation index for peak emergence time and the gap of an analyte peak emergence time from the reference peak emergence time as variable(s) with respect to the m search sets.

15. The chromatogram analyzer according to claim 1, 2, 4 or 5, wherein the second arithmetic means selects one peak identification result on the basis of the result of evaluation using an evaluation function having at least one of the peak widths, the uniformity of peak heights or peak areas, the correlation index for the peak emergence time and the gap from the standard peak time as variable(s) with respect to the m search sets.

16. The chromatogram analyzer according to claim 14, wherein the second arithmetic means selects one peak identification result on the basis of the result of evaluation obtained by substituting a predetermined constant for a variable in the evaluation function, if no peak is matched to an analyte.

17. The chromatogram analyzer according to claim 16, wherein the constant is so determined that the evaluation function gives a poor evaluation result when no peak is matched with an analyte than when a peak is matched with an analyte.

18. The chromatogram analyzer according to claim 14, wherein the second arithmetic means selects one peak identification result on the basis of the result of evaluation using an evaluation function selected from plural evaluation functions according to the number of matched analyte peaks.

19. The chromatogram analyzer according to claim 18, wherein the plural evaluation functions are so determined that the evaluation functions for fewer analytes give poor evaluation results than those for more analytes.

20. The chromatogram analyzer according to claims 1 or 4, which analyzes a chromatogram obtained by applying a sample containing at least three analytes to chromatography and further comprises a third storage means which stores the standard peak emergence time of each analyte, a fourth arithmetic means which determines an index of correlation between the stored standard peak emergence times and the peak emergence time of identified analyze peaks, and a display means which displays the degree of correlation.

21. A chromatogram analyzer which analyzes a chromatogram obtained by applying a sample containing at least three analytes, which comprises a second storage means which stores the chromatogram, a first arithmetric means which detects peaks in the chromatogram and identifies the peaks as attributable to the analytes, a third storage means which stores the reference peak emergence time of each analyte, a fourth arithmetic means which determines the indices of correlation between the stored reference peak emergence times and the emergence times of the identified analyte peaks, and a display means which displays the degree of correlation.

22. The chromatogram analyzer according to claim 21, wherein the third storage means stores standard peak emergence times at which analyte peaks are estimated to emerge, as reference peak emergence times.

23. The chromatogram analyzer according to claim 22, wherein the standard peak emergence times are measured from a chromatogram obtained by applying a standard sample containing the analytes to chromatography.

24. The chromatogram analyzer according to claim 21, wherein the fourth arithmetic means obtains the correlation coefficient or the square of the correlation coefficient as the index of correlation between reference peak emergence times and the emergence times of identified analytes peaks.

25. The chromatogram analyzer according to claim 21, wherein the gap of the peak emergence times of the analyte peaks is defined as the distance between the linear regression line correlating the standard peak emergence times and the peak emergence times of the analyte peaks and a point expressing the peak emergence time of an identified analyte peak plotted against the corresponding reference emergence time, and the fourth arithmetic means obtains the maximum absolute gap, the average absolute gap, the standard deviation of the gaps or the variance of the gaps as the index of correlation between the reference peak emergence times and the peak emergence times of identified analyte peaks.

26. The chromatogram analyzer according to claim 21, wherein the fourth arithmetic means calculates the index of correlation between the reference peak emergence times and the emergence times of identified analyte peaks and then compares the calculated index with a standard value given for the index of correlation.

* * * * *